United States Patent
Bhattacharya et al.

(10) Patent No.: US 10,519,098 B2
(45) Date of Patent: Dec. 31, 2019

(54) AROMATIC DERIVATIVES AS ANTI-MALARIAL

(71) Applicant: Council of Scientific & Industrial Research, New Delhi (IN)

(72) Inventors: Asish Kumar Bhattacharya, Pune (IN); Eswar Kumar Aratikatla, Pune (IN); Kumkum Srivastava, Lucknow (IN); Ashan Manhas, Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 286 days.

(21) Appl. No.: 15/520,989

(22) PCT Filed: Oct. 21, 2015

(86) PCT No.: PCT/IN2015/050140
§ 371 (c)(1),
(2) Date: Apr. 21, 2017

(87) PCT Pub. No.: WO2016/063301
PCT Pub. Date: Apr. 28, 2016

(65) Prior Publication Data
US 2019/0106380 A1 Apr. 11, 2019

(30) Foreign Application Priority Data
Oct. 21, 2014 (IN) ............................ 3005-DEL/2014

(51) Int. Cl.
| | | |
|---|---|---|
| *C07C 233/73* | (2006.01) | |
| *C07C 233/18* | (2006.01) | |
| *C07C 233/22* | (2006.01) | |
| *C07C 69/612* | (2006.01) | |
| *C07C 69/618* | (2006.01) | |
| *C07C 69/92* | (2006.01) | |
| *C07C 67/08* | (2006.01) | |
| *C07C 231/02* | (2006.01) | |
| *C07D 317/60* | (2006.01) | |
| *C07F 7/18* | (2006.01) | |
| *A61P 33/06* | (2006.01) | |

(52) U.S. Cl.
CPC ............ *C07C 233/73* (2013.01); *A61P 33/06* (2018.01); *C07C 67/08* (2013.01); *C07C 69/612* (2013.01); *C07C 69/618* (2013.01); *C07C 69/92* (2013.01); *C07C 231/02* (2013.01); *C07C 233/18* (2013.01); *C07C 233/22* (2013.01); *C07D 317/60* (2013.01); *C07F 7/1804* (2013.01); *C07B 2200/09* (2013.01)

(58) Field of Classification Search
CPC ..... C07C 233/73; C07C 233/18; C07C 67/08; C07C 231/02; C07C 233/22; C07C 69/618; C07C 69/92; C07C 69/612; C07D 317/60; A61P 33/06; C07B 2200/09; C07F 7/1804
See application file for complete search history.

(56) References Cited

PUBLICATIONS

Ross, S. A., "Alkamides from the Leaves of Zanthoxylum syncarpum." Journal of natural products 68.8 (2005): 1297-1299.*
Sigma Product Information Sheet RPMI-1640, 2002. p. 1-4.*
Handbook of Pharmaceutical Excipients, Pharmaceutical Press, 2009. ProQuest Ebook Central, http://ebookcentral.proquest.com/lib/uspto-ebooks/detail.action?docID=4967873; p. 197-241.*

(Continued)

*Primary Examiner* — John M Mauro
(74) *Attorney, Agent, or Firm* — Wood, Herron & Evans, LLP

(57) ABSTRACT

The present invention discloses anti-malarial compound of formula (I) Formula (I) wherein, X is selected from O or NH; $R_1$, $R_2$, $R_3$, $R_4$ and $R_5$ is selected from H or OMe or $CH_3$, $—CH_2—O—CH_2—$ or $—CH=CH—CH=CH—$; Y is selected from O or NH and $R_6$, $R_7$ is selected from the following compounds: or pharmaceutically acceptable salts thereof, process for preparation and a pharmaceutical composition containing the same.

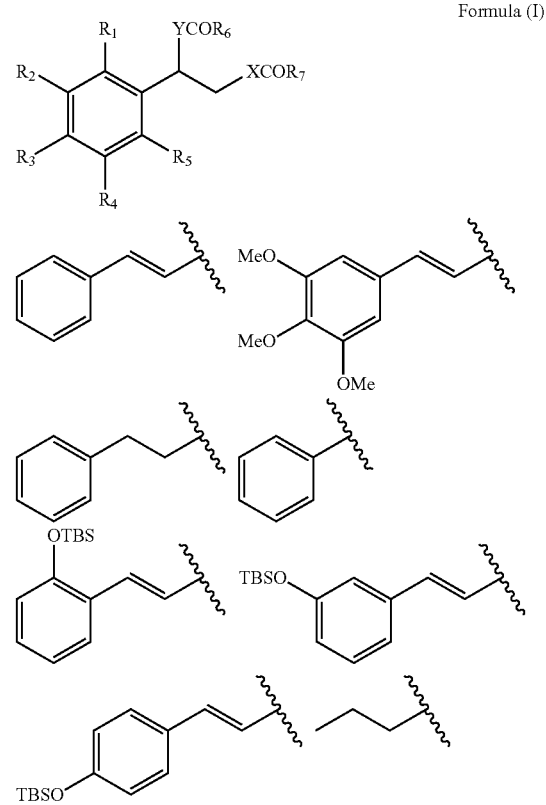

8 Claims, 1 Drawing Sheet

(56) References Cited

PUBLICATIONS

Lundell, Katri, and Liisa T. Kanerva. "Enantiomers of ring-substituted 2-amino-1-phenylethanols by Pseudomonas cepacia lipase." Tetrahedron: Asymmetry 6.9 (1995): 2281-2286.*

Souto, J. A., "Iodine (III)-Promoted Intermolecular Diamination of Alkenes." Chemistry—An Asian Journal 7.5 (2012): 1103-1111.*

Bero, J.,"Antimalarial compounds isolated from plants used in traditional medicine." Journal of Pharmacy and Pharmacology 61.11 (2009): 1401-1433.*

Hamman, Josias, and Jan Steenekamp. "Excipients with specialized functions for effective drug delivery." Expert opinion on drug delivery 9.2 (2012): 219-230.*

\* cited by examiner

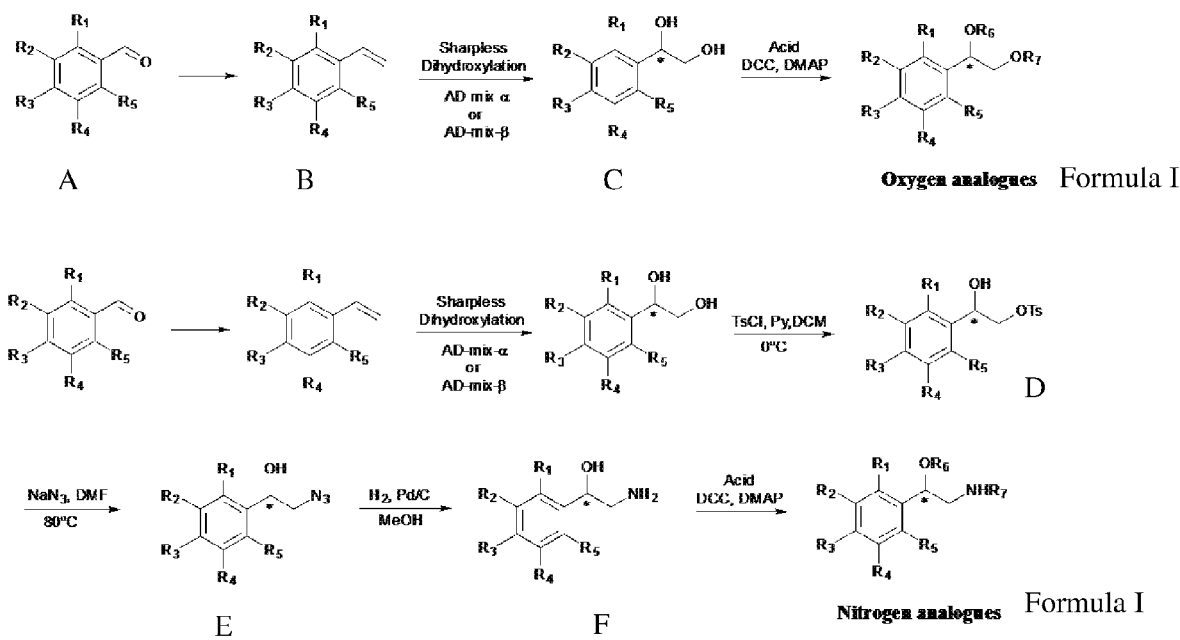

AROMATIC DERIVATIVES AS ANTI-MALARIAL

FIELD OF THE INVENTION

The present invention relates to anti-malarial compounds of formula (I) and process for preparation thereof. Particularly, the present invention relates to a pharmaceutical composition comprising compounds of formula (I) used for the treatment of malaria infection.

BACKGROUND AND PRIOR ART OF THE INVENTION

The genus *Zanthoxylum* (Rutaceae) comprises some 200 species distributed worldwide. Plants of this genus exhibit a variety of biologically active secondary metabolites including alkaloids, lignans, and coumarins with febrifuge, sudorific, and diuretic properties. Plants belonging to *Zanthoxylum syncarpum* species are not available in India but *Zanthoxylum* genus is available. Syncarpamide was not isolated from any other species of *Zanthoxylum* other than *Zanthoxylum syncarpum*.

Article titled "Syncarpamide, a new antiplasmodial (+)-norepinephrine derivative from *Zanthoxylum syncarpum*" by SA Ross et l. published in *J Nat Prod.*, 2004, 67(1), 88-90 reports a new (+)-norepinephrine derivative, syncarpamide (1), along with a known coumarin, (+)-S-marmesin (2), and one known alkaloid, decarine (3) which are isolated from the stem of *Zanthoxylum syncarpum*. They also reports syncarpamide (1) for antiplasmodial activity, with IC(50) values of 2.04 microM against *Plasmodium falciparum* D(6) clone and 3.06 microM against *P. falciparum* W(2) clone, respectively.

Article titled, "1-(3,4,5-trimethoxyphenyl)ethane-1,2-diyl esters, a novel compound class with potent chemoreversal activity" by Hsin-Yi Hung et al. published in *Bioorganic & Medicinal Chemistry Letters*, 2012, 22 (24), pp 7726-7729 reports 1-(3,4,5-trimethoxyphenyl)ethane-1,2-diyl esters, which share a fragment from (±) 3'-O-4'-O-bis(3,4-dimethoxycinnamoyl)-cis-khellactone (DMDCK) and 3'R,4'R-disubstituted-2',2'-dimethyldihydropyrano[2,3-f]chromone (DSP), which exhibits remarkable chemoreversal activity on multidrug resistant human nasopharyngeal carcinoma (KB) when combined with three anticancer drugs, paclitaxel, vincristine and doxorubicin. Among 15 novel synthesized analogs, bis-trimethoxybenzoyl derivative was the most active (340-fold more active than verapamil when used with vincristine) followed by two di-cinnamoyl derivatives, and then di-cyclohexanecarbonyl derivative.

Article titled, "Identification from a Combinatorial Library of a Small Molecule that Selectively Induces Apoptosis in Cancer Cells" by V Nesterenko et al. published in, *J. Am. Chem. Soc.*, 2003, 125 (48), pp 14672-14673 reports the synthesis of a 88-membered combinatorial library, and the subsequent evaluation of these compounds for their ability to selectively induce apoptosis in cancerous cells.

Article titled, "Shahidine, a novel and highly labile oxazoline from *Aegle marmelos*: the parent compound of aegeline and related amides" by Shaheen Faizi et al in *Tetrahedron*, 2009, 65 (5), pp 998-1004 reports a rare alkaloid, shahidine having an unstable oxazoline core isolated as a major constituent from the fresh leaves of Aeglemarmelos. Biogenetically, oxazolines may be considered as the precursor of hydroxy amides and oxazoles found in plants. Shahidine showed activity against a few Gram-positive bacteria.

Hence, it is a need to develop novel anti-malarial compounds and chemical route of synthesis known for this compound, to overcome the drawbacks of isolation process which is a multi step process with very poor yields. Accordingly, the present invention provides novel anti-malarial compounds of formula (I) and process for preparation thereof.

OBJECTIVE OF INVENTION

The main objective of the present invention is to provide anti-malarial compounds of formula (I) or pharmaceutically acceptable salts thereof.

Another objective of the present invention is to provide a process for the preparation of anti-malarial compounds of formula (I).

Still another objective of the present invention is to provide a pharmaceutical composition comprising compound of formula (I) and at least one pharmaceutically acceptable excipient.

SUMMARY OF THE INVENTION

Accordingly, present invention provides anti-malarial compound of formula (I)

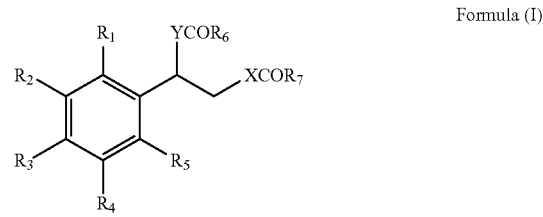

Formula (I)

wherein, X is selected from O or NH;

$R_1$, $R_2$, $R_3$, $R_4$ and $R_5$ is selected from H, $CH_3$ or OMe, or $R_1$ and $R_2$ or $R_2$ and $R_3$ or $R_3$ and $R_4$ or $R_4$ and $R_5$ may combined to form 5 to 6 membered saturated or unsaturated ring optionally having one or more hetero atoms;

Y is selected from O or NH and $R_6$, $R_7$ is selected from

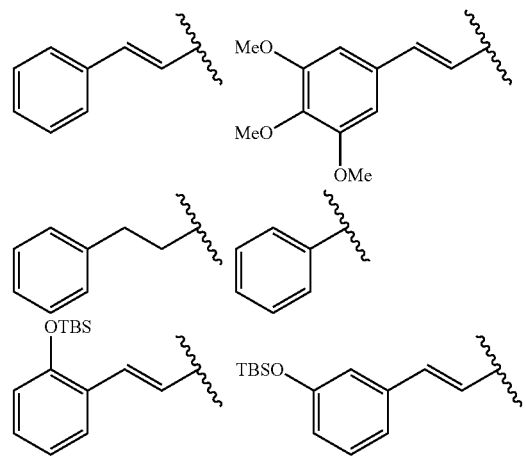

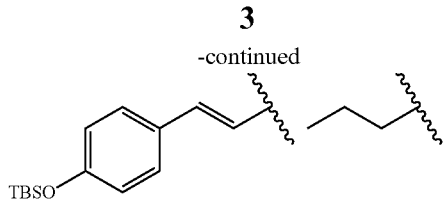

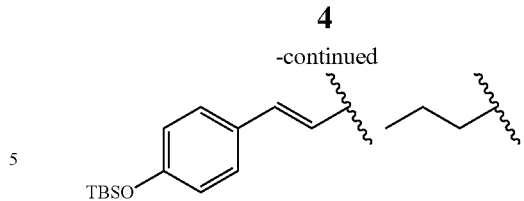

or pharmaceutically acceptable salts thereof.

BRIEF DESCRIPTION OF THE DRAWINGS

The accompanying drawings, which are incorporated in and constitute a part of this specification, illustrate embodiments of the invention and, together with the general description of the invention given above and the detailed description of the embodiments given below, serve to explain the principles of the present invention.

FIG. 1 is a schematic showing a process for the preparation of an anti-malarial compound of formula (I).

DETAILED DESCRIPTION OF THE INVENTION

Present invention provides compound of formula (I)

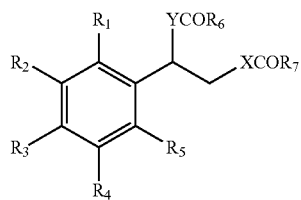

Formula (I)

wherein, X is selected from O or NH;

$R_1$, $R_2$, $R_3$, $R_4$ and $R_5$ is selected from H, $CH_3$ or OMe, or $R_1$ and $R_2$ or $R_2$ and $R_3$ or $R_3$ and $R_4$ or $R_4$ and $R_5$ may combined to form 5 to 6 membered saturated or unsaturated ring optionally having one or more hetero atoms;

Y is selected from O or NH and $R_6$, $R_7$ is selected from

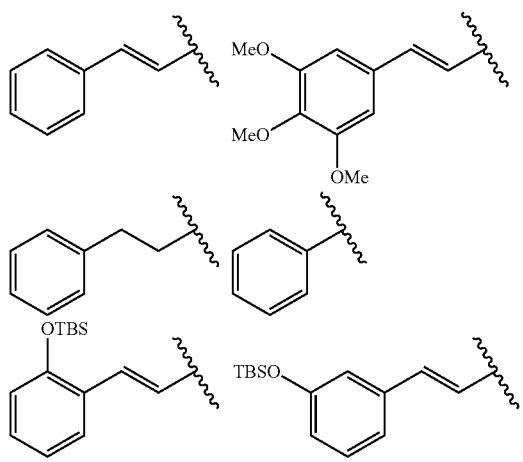

or pharmaceutically acceptable salts thereof.

In an embodiment of the present invention, compound of formula (I) are selected from (S)-2-cinnamamido-1-(3,4-dimethoxyphenyl)ethyl cinnamate (1),
(R)-2-cinnamamido-1-(3,4-dimethoxyphenyl)ethylcinnamate (2),
(S)-1-(3,4-dimethoxyphenyl)ethane-1,2-diyl(2E,2'E)-bis(3-phenylacrylate) (3),
(R)-1-(3,4-dimethoxyphenyl)ethane-1,2-diyl(2E,2'E)-bis(3-phenylacrylate)(4),
(S)-2-cinnamamido-1-(3,4,5-trimethoxyphenyl) ethyl cinnamate (5),
(R)-2-cinnamamido-1-(3,4,5-trimethoxyphenyl)ethyl cinnamate (6),
(S)-1-(3,4,5-trimethoxyphenyl)ethane-1,2-diyl (2E,2'E)-bis (3-phenylacrylate) (7),
(R)-1-(3,4,5-trimethoxyphenyl)ethane-1,2-diyl(2E,2'E)-bis (3-phenylacrylate) (8),
(S)-2-cinnamamido-1-(2-methoxyphenyl)ethylcinnamate (9),
(R)-2-cinnamamido-1-(2-methoxyphenyl)ethylcinnamate (10),
(S)-1-(2-methoxyphenyl)ethane-1,2-diyl(2E,2'E)-bis(3-phenylacrylate)(11),
(R)-1-(2-methoxyphenyl)ethane-1,2-diyl(2E,2'E)-bis(3-phenylacrylate) (12),
(S)-2-cinnamamido-1-(3-methoxyphenyl)ethyl cinnamate (13),
(R)-2-cinnamamido-1-(3-methoxyphenyl)ethylcinnamate (14),
(S)-1-(3-methoxyphenyl)ethane-1,2-diyl (2E,2'E)-bis(3-phenylacrylate)(15),
(R)-1-(3-methoxyphenyl)ethane-1,2-diyl(2E,2'E)-bis(3-phenylacrylate)(16),
(S)-2-cinnamamido-1-(4-methoxyphenyl)ethyl cinnamate (17),
(R)-2-cinnamamido-1-(4-methoxyphenyl)ethylcinnamate (18),
(S)-1-(4-methoxyphenyl)ethane-1,2-diyl (2E,2'E)-bis(3-phenylacrylate) (19),
(R)-1-(4-methoxyphenyl)ethane-1,2-diyl(2E,2'E)-bis(3-phenylacrylate)(20),
(S)-2-cinnamamido-1-(2,3-dimethoxyphenyl)ethyl cinnamate (21),
(R)-2-cinnamamido-1-(2,3-dimethoxyphenyl)ethyl cinnamate (22),
(S)-1-(2,3-dimethoxyphenyl)ethane-1,2-diyl(2E,2'E)-bis(3-phenylacrylate)(23),
(R)-1-(2,3-dimethoxyphenyl)ethane-1,2-diyl(2E,2'E)-bis(3-phenylacrylate)(24),
(S)-2-cinnamamido-1-phenylethyl cinnamate (25),
(R)-2-cinnamamido-1-phenylethyl cinnamate (26),
(S)-1-phenylethane-1,2-diyl(2E,2'E)-bis(3-phenylacrylate) (27),
(R)-1-phenylethane-1,2-diyl (2E,2'E)-bis(3-phenylacrylate) (28),
(S)-2-cinnamamido-1-(p-tolyl)ethyl cinnamate (29),
(R)-2-cinnamamido-1-(p-tolyl)ethylcinnamate (30), (S)-1-(p-tolyl)ethane-1,2-diyl (2E,2'E)-bis(3-phenylacrylate)(31),
(R)-1-(p-tolyl)ethane-1,2-diyl(2E,2'E)-bis(3-phenylacrylate) (32),
(S)-1-(benzo[d][1,3]dioxol-5-yl)-2-cinnamamidoethylcinnamate (33),
(R)-1-(benzo[d][1,3]dioxol-5-yl)-2-cinnamamidoethylcinnamate (34),
(S)-1-(benzo[d][1,3]dioxol-5-yl)ethane-1,2-diyl(2E,2'E)-bis(3-phenylacrylate)(35),
(R)-1-(benzo[d][1,3]dioxol-5-yl)ethane-1,2-diyl (2E,2'E)-bis(3-phenylacrylate) (36),
(S)-1-(benzo[d][1,3]dioxol-4-yl)ethane-1,2-diyl (2E,2'E)-bis(3-phenylacrylate) (37),
(R)-1-(benzo[d][1,3]dioxol-4-yl)ethane-1,2-diyl (2E,2'E)-bis(3-phenylacrylate)(38),
(S)-2-benzamido-1-(3,4-dimethoxyphenyl)ethyl benzoate (39),
(R)-2-benzamido-1-(3,4-dimethoxyphenyl)ethyl benzoate (40),
(S)-1-(3,4-dimethoxyphenyl)-2-((E)-3-(3,4,5-trimethoxyphenyl)acrylamido)ethyl(E)-3-(3,4,5-trimethoxyphenyl)acrylate (41),
(R)-1-(3,4-dimethoxyphenyl)-2-((E)-3-(3,4,5-trimethoxyphenyl)acrylamido)ethyl(E)-3-(3,4,5-trimethoxyphenyl)acrylate (42),
(S)-1-(3,4-dimethoxyphenyl)-2-(3-phenylpropanamido)ethyl3-phenylpropanoate (43),
(R)-1-(3,4-dimethoxyphenyl)-2-(3-phenylpropanamido)ethyl3-phenylpropanoate (44),
(S)-2-utyramido-1-(3,4-dimethoxyphenyl)ethylbutyrate (45),
(S)-2-((E)-3-(2-((tert-butyldimethylsilyl)oxy)phenyl)acrylamido)-1-(3,4-dimethoxyphenyl)ethyl(E)-3-(2-((tert-butyldimethylsilyl)oxy)phenyl)acrylate (46);
(S)-2-((E)-3-(3-((tert-utyldimethylsilyl)oxy)phenyl)acrylamido)-1-(3,4-dimethoxyphenyl)ethyl(E)-3-(3-((tert-butyldimethylsilyl)oxy)phenyl)acrylate (47),
(S)-2-((E)-3-(4-((tert-butyldimethylsilyl)oxy)phenyl)acrylamido)-1-(3,4-dimethoxy phenyl)ethyl(E)-3-(4-((tert-butyldimethylsilyl)oxy)phenyl)acrylate (48),
(S)-2-cinnamamido-1-(3,4-dimethoxyphenyl)ethyl3-phenylpropanoate (49),
(S)-1-(3,4-dimethoxyphenyl)-2-(3-phenylpropanamido)ethylcinnamate (50),
(S)-2-butyramido-1-(3,4-dimethoxyphenyl)ethylcinnamate (51),
(S)-2-cinnamamido-1-(3,4-dimethoxyphenyl)ethyl butyrate (52),
(S)-1-(naphthalen-2-yl)ethane-1,2-diyl (2E,2'E)-bis(3-phenylacrylate) (53),
(R)-1-(naphthalen-2-yl)ethane-1,2-diyl (2E,2'E)-bis(3-phenylacrylate) (54),
(S)-2-cinnamamido-2-(3,4-dimethoxyphenyl)ethylcinnamate (55),
(S)-1-(3,4-dimethoxyphenyl)ethane-1,2-diyl(2E,2'E)-bis(3-(3,4,5-trimethoxyphenyl)acrylate)(56),
(S)-1-(3,4,5-trimethoxyphenyl)ethane-1,2-diyl(2E,2'E)-bis(3-(3,4,5-trimethoxyphenyl)acrylate)(57),
(S)-1-(3,4,5-trimethoxyphenyl)-2-((E)-3-(3,4,5-trimethoxyphenyl)acrylamido)ethyl(E)-3-(3,4,5-trimethoxyphenyl)acrylate (58).

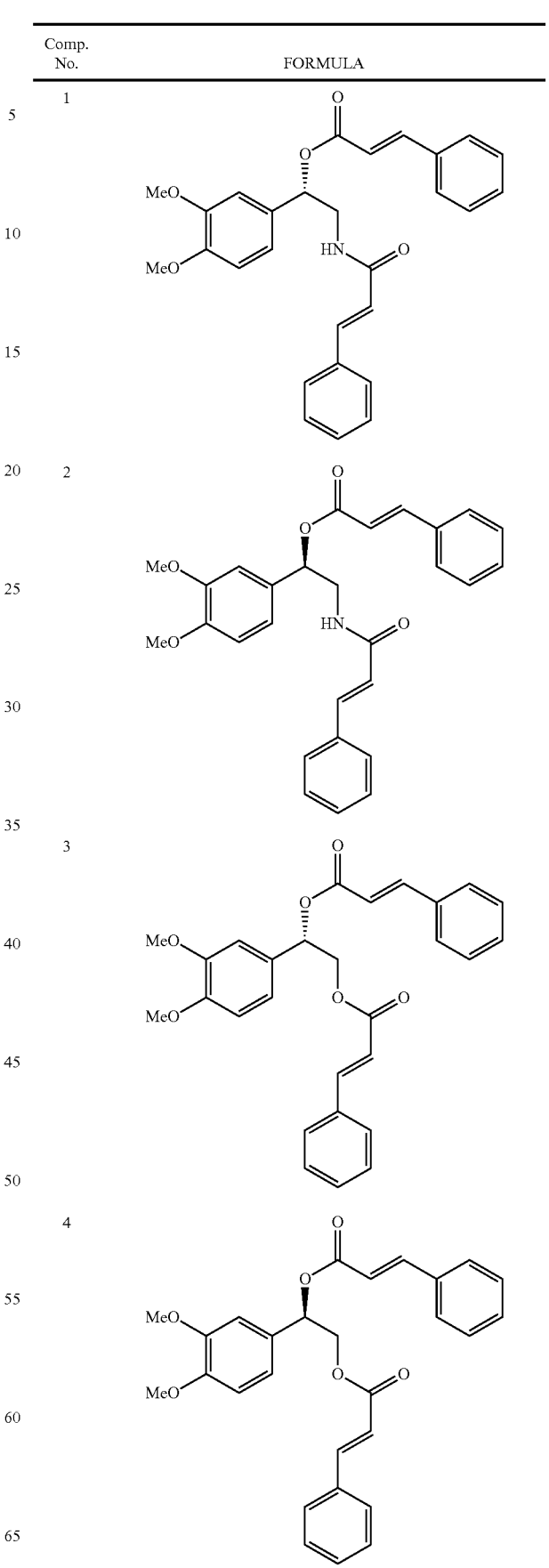

| Comp. No. | FORMULA |
|---|---|
| 1 | |
| 2 | |
| 3 | |
| 4 | |

-continued
| Comp. No. | FORMULA |
|---|---|
| 5 | 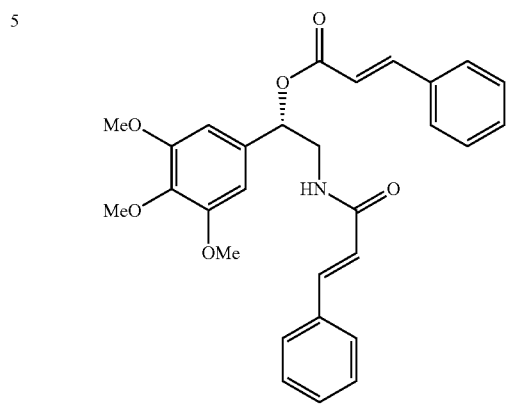 |
| 6 | 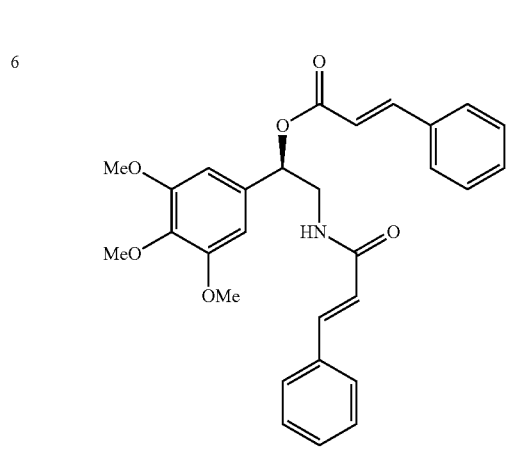 |
| 7 | 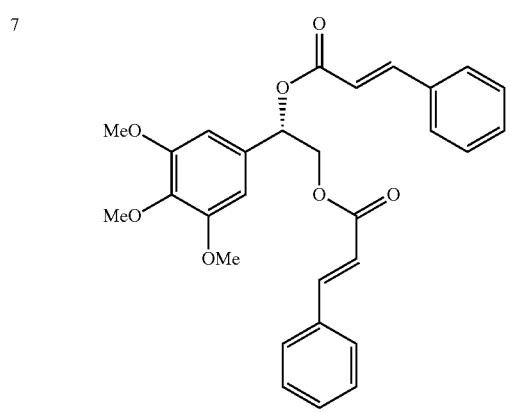 |
-continued
| Comp. No. | FORMULA |
|---|---|
| 8 | 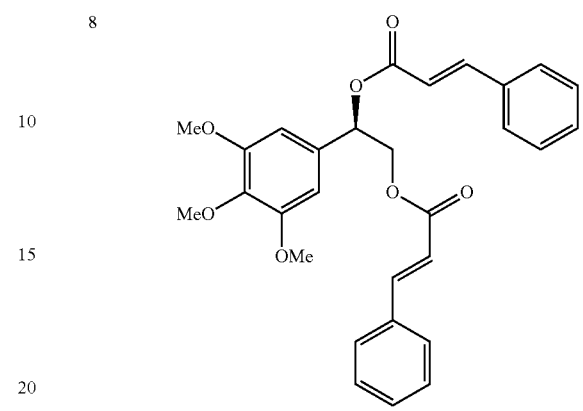 |
| 9 | 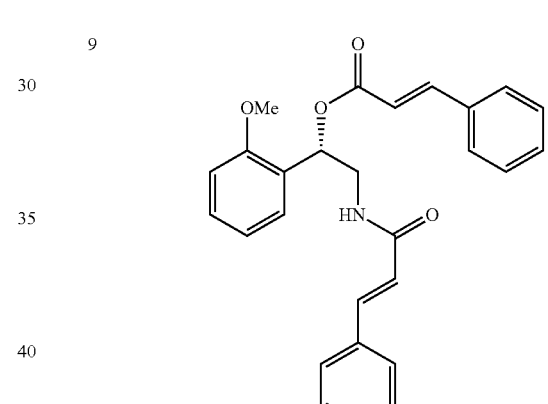 |
| 10 | 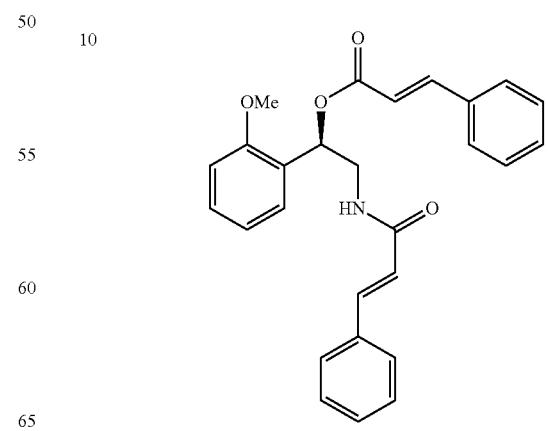 |

-continued
| Comp. No. | FORMULA |
|---|---|
| 11 | 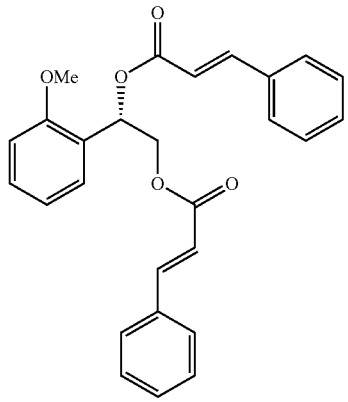 [SMILES: COc1ccccc1[C@@H](COC(=O)/C=C/c1ccccc1)OC(=O)/C=C/c1ccccc1] |
| 12 | 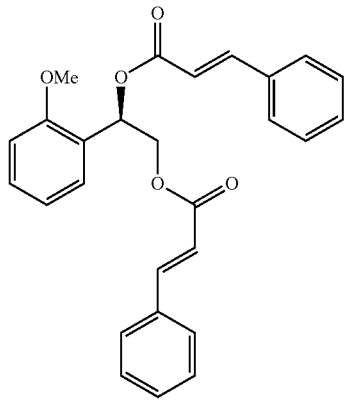 |
| 13 | 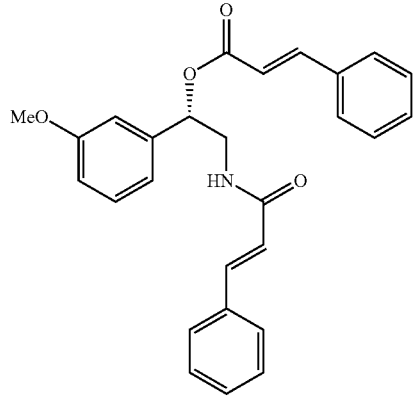 [SMILES: COc1cccc([C@@H](CNC(=O)/C=C/c2ccccc2)OC(=O)/C=C/c2ccccc2)c1] |
-continued
| Comp. No. | FORMULA |
|---|---|
| 14 | 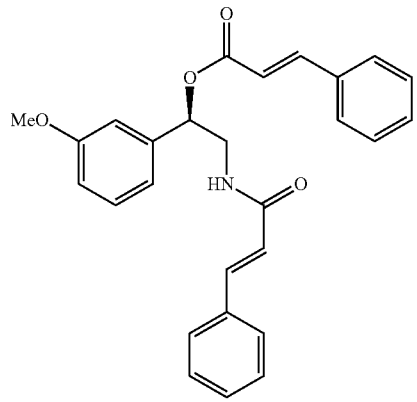 [SMILES: COc1cccc([C@H](CNC(=O)/C=C/c2ccccc2)OC(=O)/C=C/c2ccccc2)c1] |
| 15 | 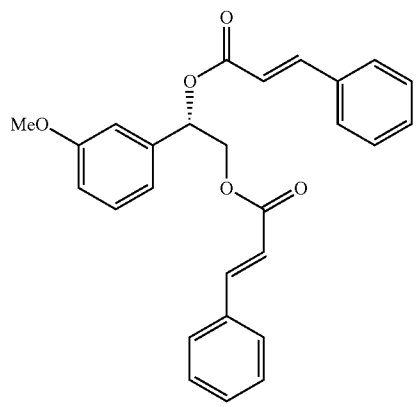 [SMILES: COc1cccc([C@@H](COC(=O)/C=C/c2ccccc2)OC(=O)/C=C/c2ccccc2)c1] |
| 16 | 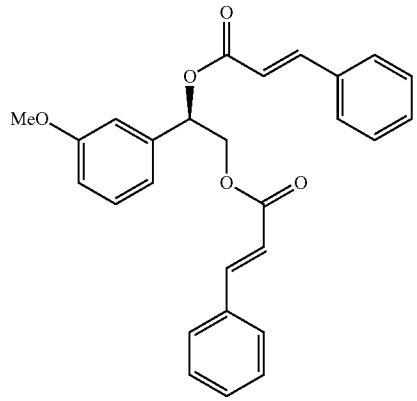 [SMILES: COc1cccc([C@H](COC(=O)/C=C/c2ccccc2)OC(=O)/C=C/c2ccccc2)c1] |

-continued
| Comp. No. | FORMULA |
|---|---|
| 17 | 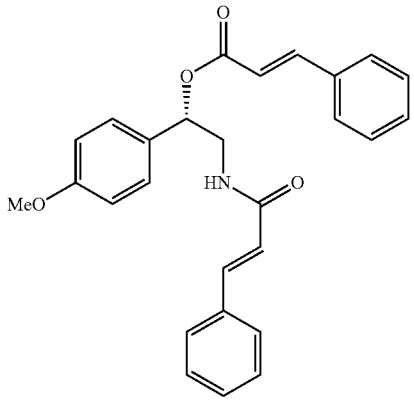 [SMILES: COc1ccc([C@@H](CNC(=O)/C=C/c2ccccc2)OC(=O)/C=C/c2ccccc2)cc1] |
| 18 | 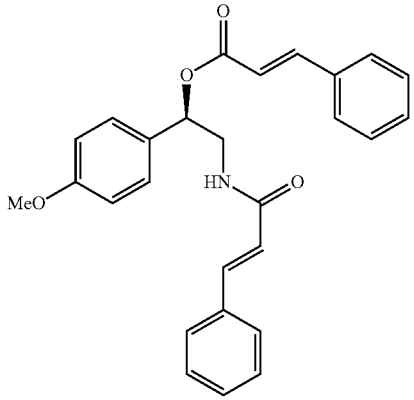 [SMILES: COc1ccc([C@H](CNC(=O)/C=C/c2ccccc2)OC(=O)/C=C/c2ccccc2)cc1] |
| 19 | 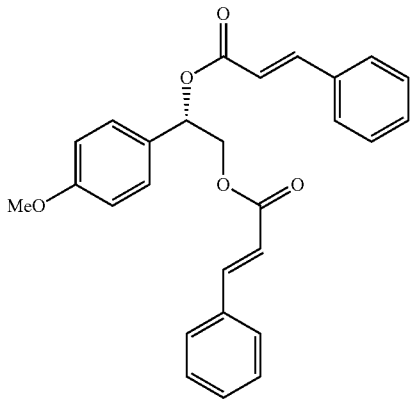 [SMILES: COc1ccc([C@@H](COC(=O)/C=C/c2ccccc2)OC(=O)/C=C/c2ccccc2)cc1] |
-continued
| Comp. No. | FORMULA |
|---|---|
| 20 | 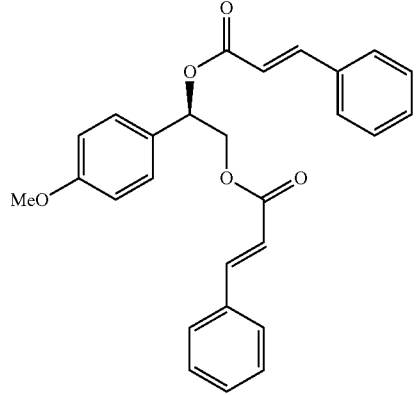 [SMILES: COc1ccc([C@H](COC(=O)/C=C/c2ccccc2)OC(=O)/C=C/c2ccccc2)cc1] |
| 21 | |
| 22 | 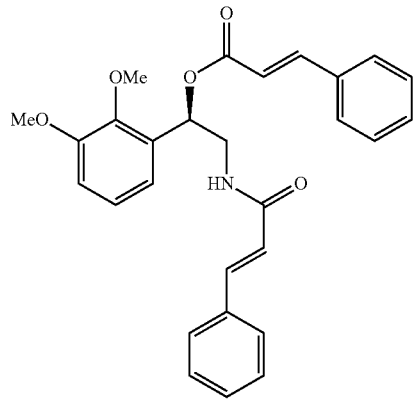 [SMILES: COc1cccc([C@H](CNC(=O)/C=C/c2ccccc2)OC(=O)/C=C/c2ccccc2)c1OC] |

-continued
| Comp. No. | FORMULA |
|---|---|
| 23 | 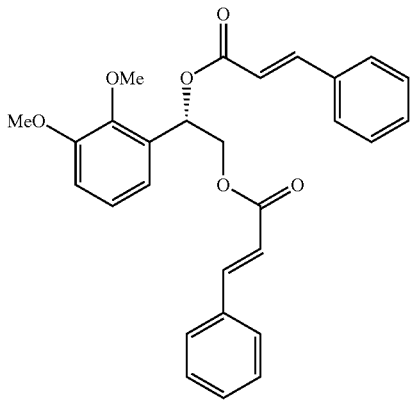 [SMILES: COc1cccc([C@@H](COC(=O)/C=C/c2ccccc2)OC(=O)/C=C/c2ccccc2)c1OC] |
| 24 | 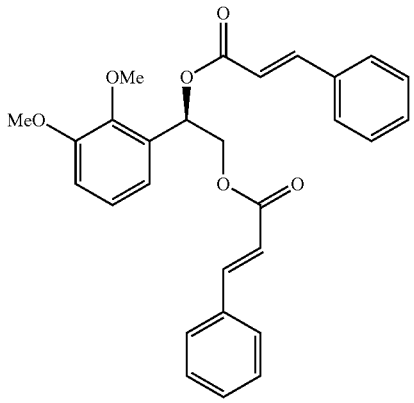 [SMILES: COc1cccc([C@H](COC(=O)/C=C/c2ccccc2)OC(=O)/C=C/c2ccccc2)c1OC] |
| 25 | 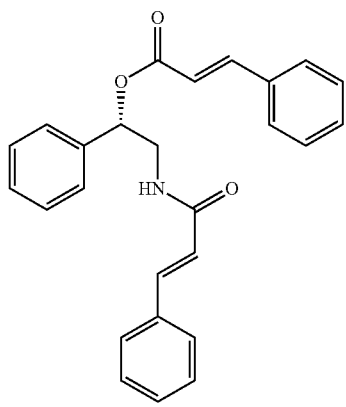 [SMILES: O=C(/C=C/c1ccccc1)OC[C@@H](OC(=O)/C=C/c1ccccc1)c1ccccc1] |
-continued
| Comp. No. | FORMULA |
|---|---|
| 26 | 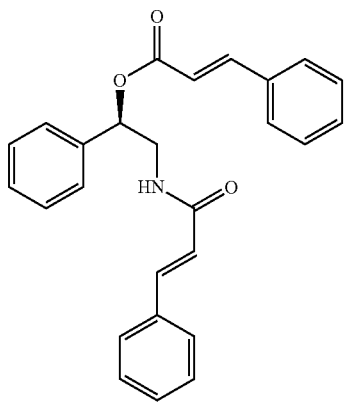 [SMILES: O=C(/C=C/c1ccccc1)OC[C@H](OC(=O)/C=C/c1ccccc1)c1ccccc1] |
| 27 | 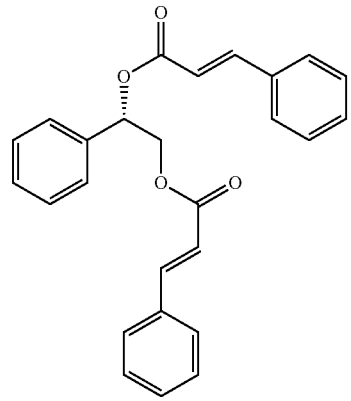 |
| 28 | 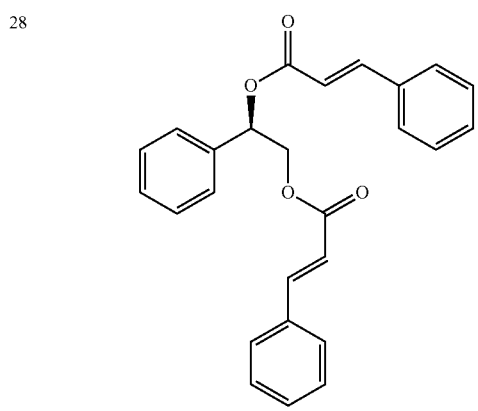 |

-continued
| Comp. No. | FORMULA |
|---|---|
| 29 | 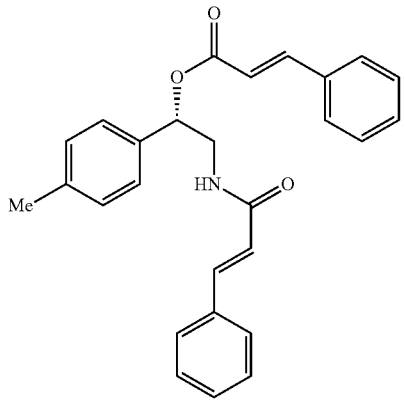 [SMILES: Cc1ccc([C@@H](CNC(=O)/C=C/c2ccccc2)OC(=O)/C=C/c2ccccc2)cc1] |
| 30 | 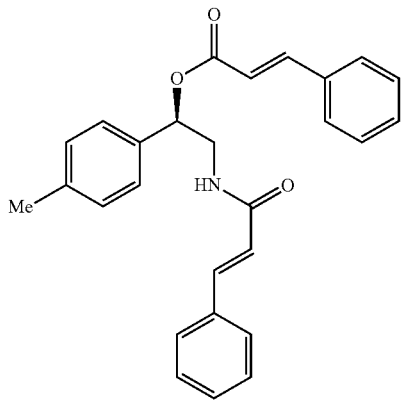 [SMILES: Cc1ccc([C@H](CNC(=O)/C=C/c2ccccc2)OC(=O)/C=C/c2ccccc2)cc1] |
| 31 | 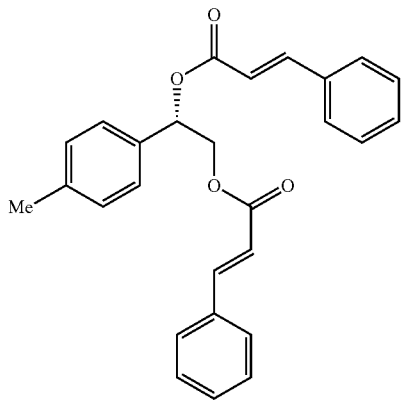 [SMILES: Cc1ccc([C@@H](COC(=O)/C=C/c2ccccc2)OC(=O)/C=C/c2ccccc2)cc1] |
-continued
| Comp. No. | FORMULA |
|---|---|
| 32 | 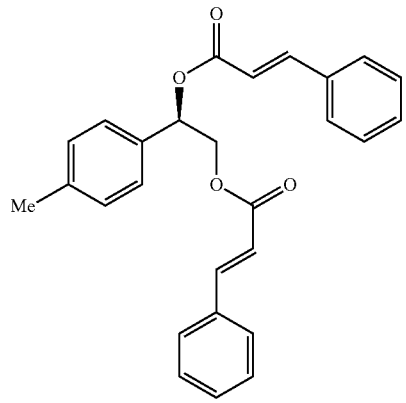 [SMILES: Cc1ccc([C@H](COC(=O)/C=C/c2ccccc2)OC(=O)/C=C/c2ccccc2)cc1] |
| 33 | 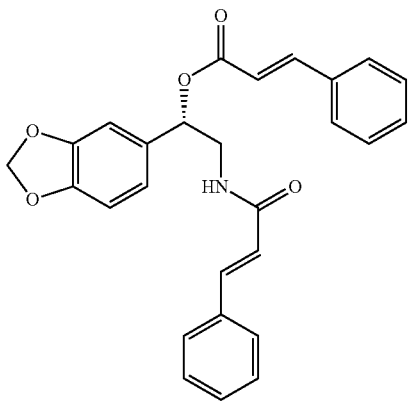 |
| 34 | 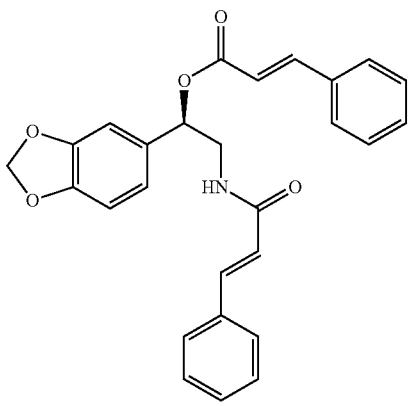 |

-continued
| Comp. No. | FORMULA |
|---|---|
| 35 | 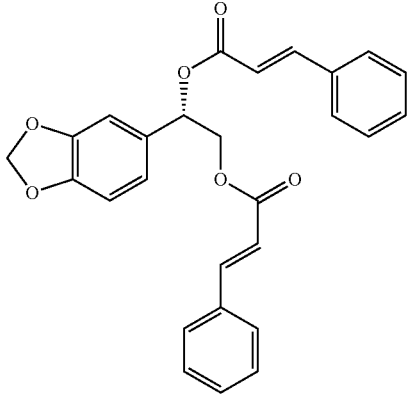 [SMILES: O=C(/C=C/c1ccccc1)OC[C@@H](OC(=O)/C=C/c1ccccc1)c1ccc2c(c1)OCO2] |
| 36 | 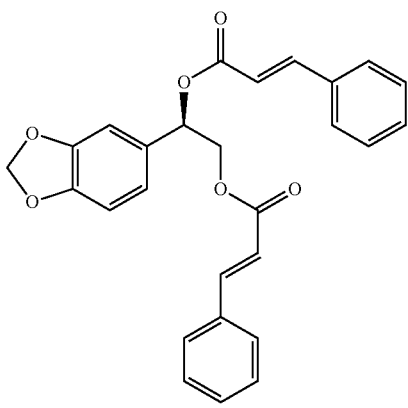 [SMILES: O=C(/C=C/c1ccccc1)OC[C@H](OC(=O)/C=C/c1ccccc1)c1ccc2c(c1)OCO2] |
| 37 | 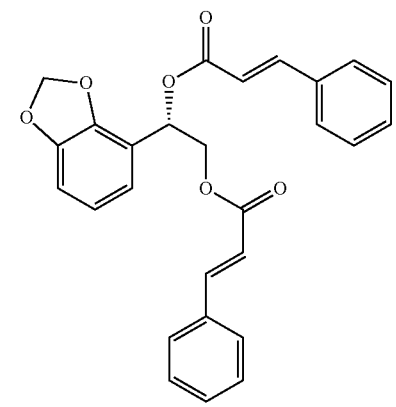 [SMILES: O=C(/C=C/c1ccccc1)OC[C@@H](OC(=O)/C=C/c1ccccc1)c1cccc2c1OCO2] |
-continued
| Comp. No. | FORMULA |
|---|---|
| 38 | 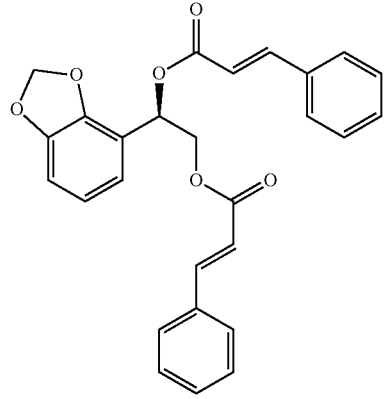 [SMILES: O=C(/C=C/c1ccccc1)OC[C@H](OC(=O)/C=C/c1ccccc1)c1cccc2c1OCO2] |
| 39 | 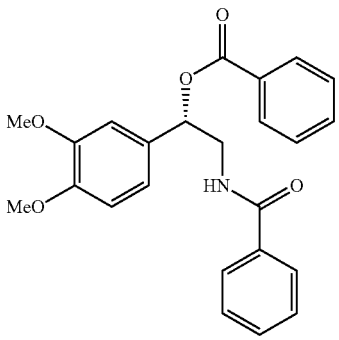 [SMILES: COc1ccc([C@@H](CNC(=O)c2ccccc2)OC(=O)c2ccccc2)cc1OC] |
| 40 | |
| 41 | 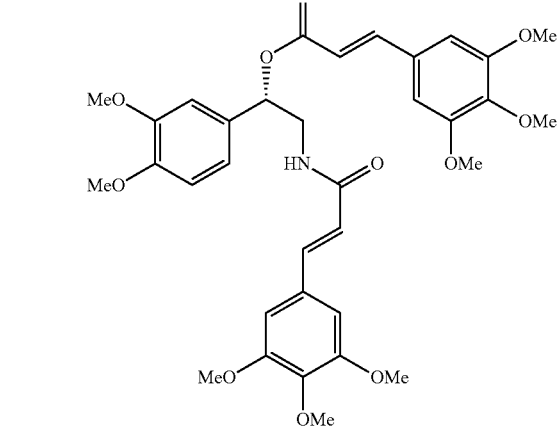 |

-continued
| Comp. No. | FORMULA |
|---|---|
| 42 | 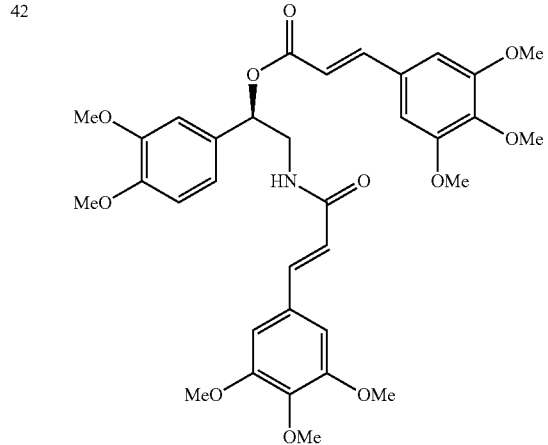 |
| 43 | 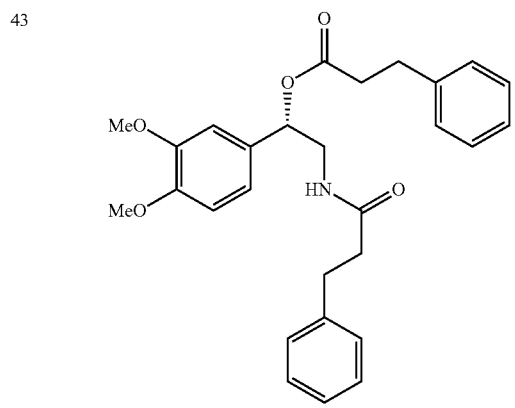 |
| 44 | 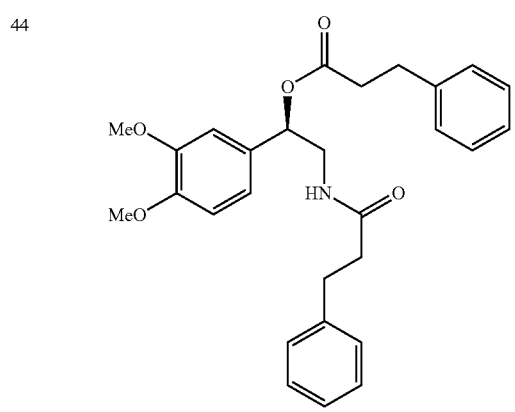 |
| 45 | 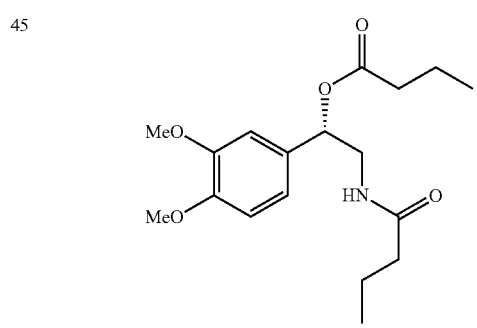 |
-continued
| Comp. No. | FORMULA |
|---|---|
| 46 | 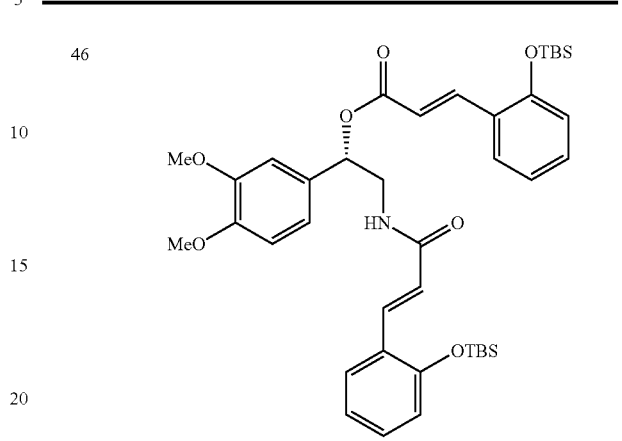 |
| 47 | 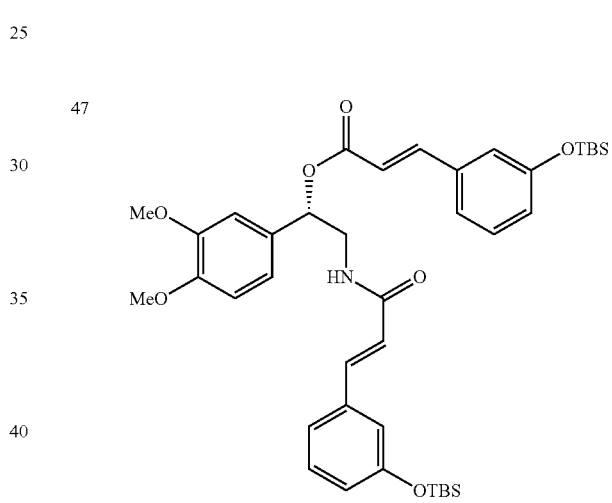 |
| 48 | |

| Comp. No. | FORMULA |
|---|---|
| 49 | 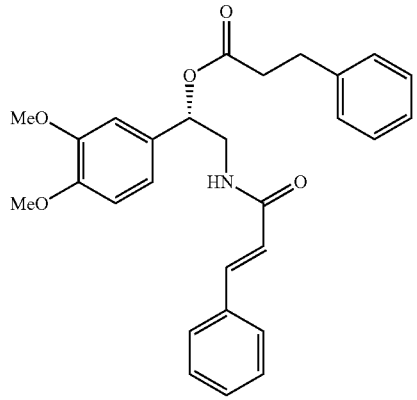 [SMILES: COc1ccc([C@@H](CNC(=O)/C=C/c2ccccc2)OC(=O)CCc2ccccc2)cc1OC] |
| 50 | 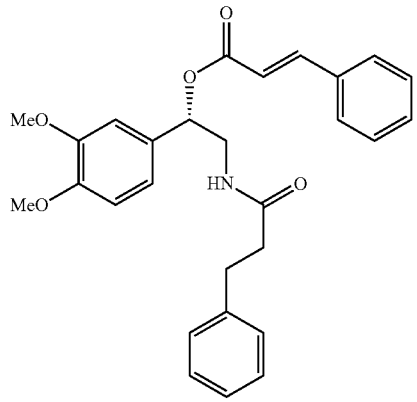 [SMILES: COc1ccc([C@@H](CNC(=O)CCc2ccccc2)OC(=O)/C=C/c2ccccc2)cc1OC] |
| 51 | 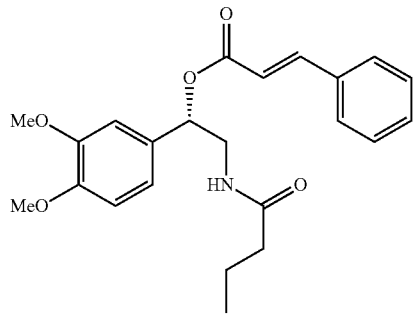 [SMILES: CCCC(=O)NC[C@@H](OC(=O)/C=C/c1ccccc1)c1ccc(OC)c(OC)c1] |
| 52 | 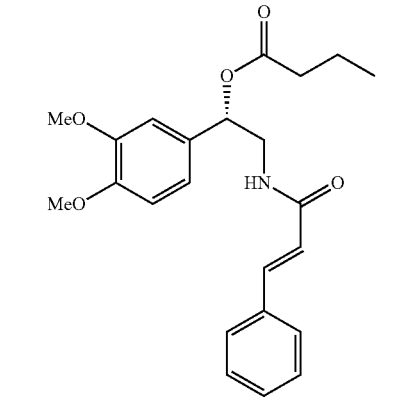 [SMILES: CCCC(=O)O[C@H](CNC(=O)/C=C/c1ccccc1)c1ccc(OC)c(OC)c1] |
| Comp. No. | FORMULA |
|---|---|
| 53 | 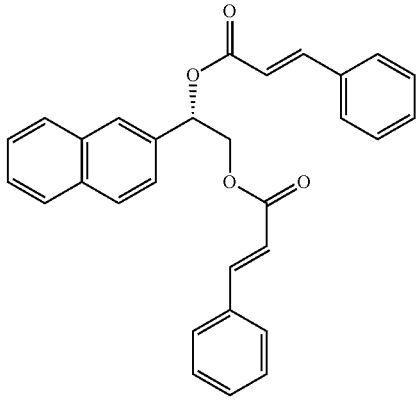 [SMILES: O=C(/C=C/c1ccccc1)OC[C@@H](OC(=O)/C=C/c1ccccc1)c1ccc2ccccc2c1] |
| 54 | 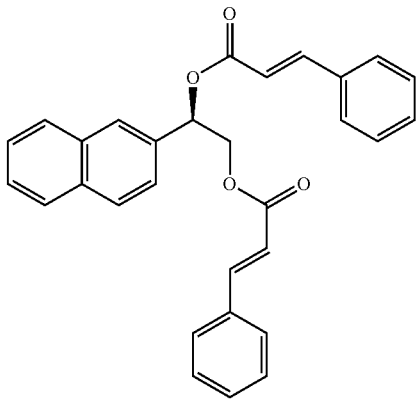 [SMILES: O=C(/C=C/c1ccccc1)OC[C@H](OC(=O)/C=C/c1ccccc1)c1ccc2ccccc2c1] |
| 55 | 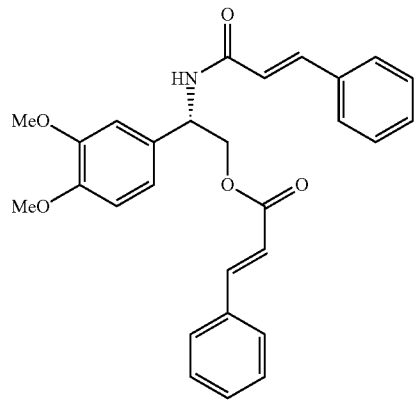 [SMILES: COc1ccc([C@@H](COC(=O)/C=C/c2ccccc2)NC(=O)/C=C/c2ccccc2)cc1OC] |

| Comp. No. | FORMULA |
|---|---|
| 56 | 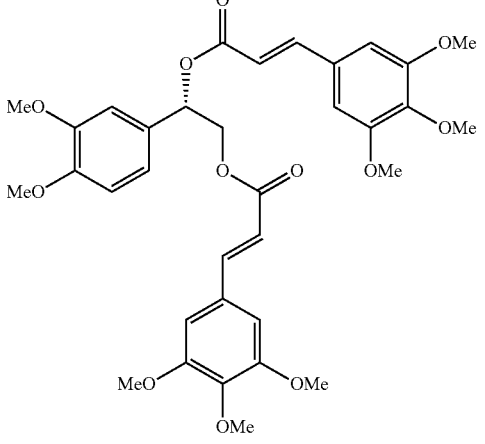 |
| 57 | 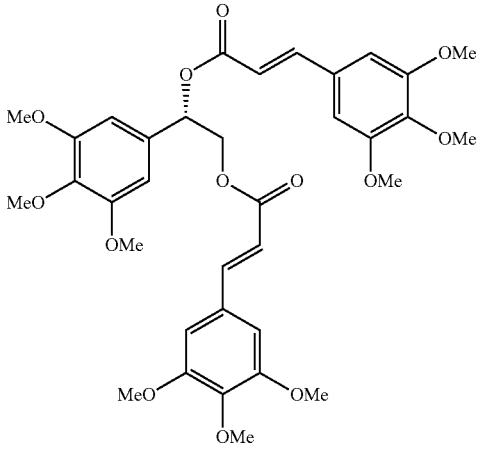 [SMILES: COc1cc(/C=C/C(=O)OC[C@@H](OC(=O)/C=C/c2cc(OC)c(OC)c(OC)c2)c2cc(OC)c(OC)c(OC)c2)cc(OC)c1OC] |
| 58 | 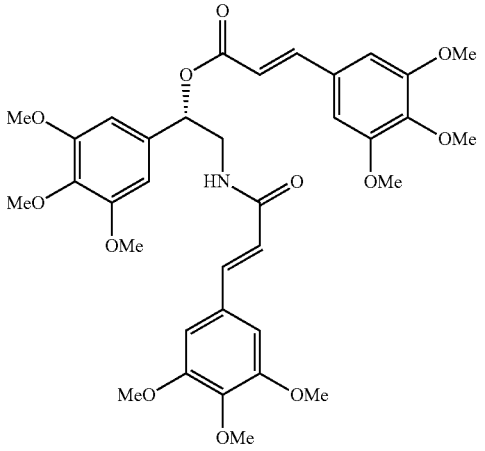 [SMILES: COc1cc(/C=C/C(=O)NC[C@@H](OC(=O)/C=C/c2cc(OC)c(OC)c(OC)c2)c2cc(OC)c(OC)c(OC)c2)cc(OC)c1OC] |

In yet another embodiment of the present invention, said compounds are useful as anti-malarial agents.

In yet another embodiment, present invention provides a process for the preparation of compounds of formula (I) with >70% yield wherein said process comprising the steps of:
a) subjecting the styrene compound of formula B for dihydroxylation to obtain the diol compound of formula C;
b) subjecting the diol compound of formula C of step (a) to monotosylation to obtain the monotosylated compound of formula D;
c) treating the monotosylated compound of formula D of step (b) with sodium azide to obtain the azido alcohol of formula E;
d) reducing the azido alcohol of formula E of step (c) with anhydrous MeOH and palladium on carbon to furnish the amino alcohol of formula F;
e) coupling the amino alcohol of formula F of step (d) or diol compound of formula C of step (a) with acid in presence of DCC (N,N'-dicyclohexylcarbodiimide) and DMAP (4-Dimethylaminopyridine) to obtain the compound of formula I.

In yet another embodiment of the present invention, dihydroxylation in step (a) is carried out at 0° C. for the period ranging from 6 to 24 h.

In yet another embodiment of the present invention, monotosylation in step (b) carried out at 0° C. for the period ranging from 3 to 4 h.

The above process for the preparation of compound of formula (I) is shown in FIG. 1.

In yet another embodiment of the present invention, styrene compounds of formula B in step (a) are selected from

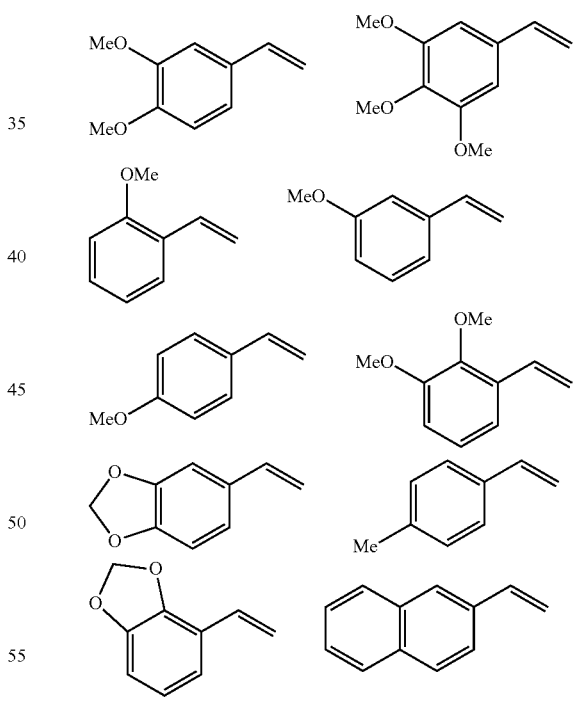

In yet another embodiment of the present invention, acid compounds in step (e) are selected from

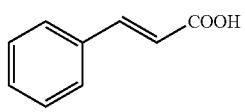

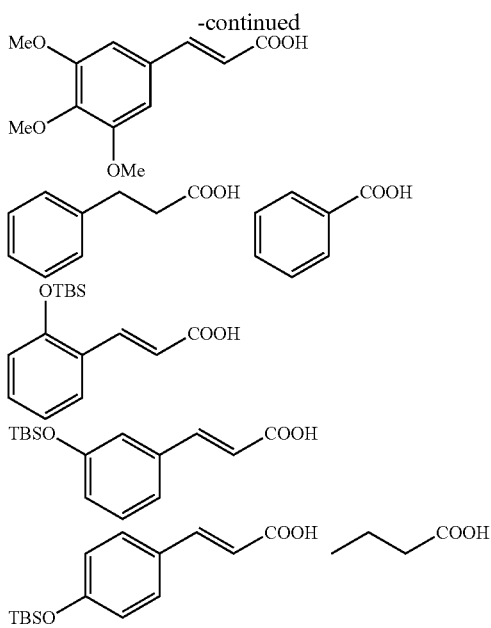

In yet another embodiment, present invention provides a pharmaceutical composition useful for the treatment of malaria infection comprising a compound of formula (I), or a stereoisomer, or ester or pharmaceutically acceptable salt thereof, and a pharmaceutically acceptable carrier, diluents or excipient.

In yet another embodiment of the present invention, the compound of formula (I) is present in the composition in an amount, which is effective to treat the infection, disease or the condition.

In yet another embodiment of the present invention, the compounds of the instant invention are effective as antiplasmodium agent and used for the treatment of malaria. They are more effective against 3D7 and K1 strains of Plasmodium falciparum (P. falciparum).

In yet another embodiment of the present invention, the compounds 1, 5, 7, 11, 41, 42, 56, 57 and 58 are more effective against 3D7 and K1 strains of Plasmodium falciparum (P. falciparum).

In yet another embodiment of the present invention, the present invention provides anti-malarial compounds 1, 5, 7, 11, 41, 42, 56, 57 and 58 with $IC_{50}$ values in the range of 2 to 7 (µg/mL)/(µM) against 3D7 culture and in the range of 1.5 to 4 (µg/mL)/(µM) against K1 culture.

In yet another embodiment, present invention provides anti-malarial compounds 1, 5, 7, 11, 41, 42, 56, 57 and 58 with $CC_{50}$ values are 80.66, 66.74, 6.44, 14.04, 87.98, 88.94, 55.70, 47.38, 42.68 (µg/mL)/(µM) respectively.

In yet another embodiment, present invention provides a pharmaceutical composition prepared by combining a compound of the invention with an appropriate pharmaceutically acceptable carrier, diluents or excipient, and may be formulated into preparations in solid, semi-solid, liquid or gaseous forms, such as tablets, capsules, powders, granules, ointments, solutions, injections, gels and microspheres, In yet another embodiment, present invention provides pharmaceutical compositions of the invention formulated so as to allow the active ingredients contained therein to be bioavailable upon administration of the composition to a patient. The compositions that will be administered to a subject or patient may take the form of one or more dosage units. The dosage forms can also be prepared as sustained, controlled, modified and immediate dosage forms.

In yet another embodiment of the present invention, the compounds of the present invention can also be administered optionally with other actives depending on the disease conditions.

As used herein the term "therapeutically effective amount" means an amount used in the pharmaceutical preparations to achieve the desired therapeutic effect.

The amount/quantity of the compound used in pharmaceutical compositions of the present invention will vary depending upon the body weight of the patient and the mode of administration and can be of any effective amount to achieve the desired therapeutic effect.

In yet another embodiment, present invention provides a method for treating or preventing a malaria infection in a subject, which comprises administering a therapeutically effective amount of the compound of formula (I) in association with at least one pharmaceutical acceptable carrier, diluents or excipient, wherein said subject is human.

In yet another embodiment, present invention relates to administering 'an effective amount' of the 'composition of invention' to the subject suffering from said disease. Accordingly, compound of formula (I) and pharmaceutical compositions containing them may be administered using any amount, any form of pharmaceutical composition via any route of administration effective for treating the disease. Typical routes of administering such pharmaceutical compositions include, without limitation, oral, topical, transdermal, inhalation, parenteral, sublingual, buccal, rectal, vaginal, and intranasal.

EXAMPLES

The following examples are given by way of illustration and therefore should not be construed to limit the scope of the invention.

a) General Procedure for the Synthesis of Substituted Styrenes Compound of Formula B To a stirred suspension of methyltriphenylphosphonium bromide in THF, base (inorganic base like NaH, NaNH$_2$ or organic base like n-BuLi) was added under argon at 0° C. and stirred for 30 min. After the mixture was cooled again to 0° C., aromatic aldehyde compound of formula A in THF was added drop wise and stirred for 12 h. The mixture was concentrated under vacuo and residue was dissolved in water and aqueous layer was extracted with DCM (3×35 mL). The combined organic extracts were dried over anhydrous Na$_2$SO$_4$, concentrated and purified by silica gel column chromatography in hexane:ethyl acetate (95:5) to afford pure styrene.

b) General Procedure for Dihydroxylation of Styrenes:

A round-bottomed flask, equipped with a magnetic stirrer, was charged with 5 mL of tert-butyl alcohol, 5 mL of water, and 1.4 g of AD-mix-α or AD-mix-β. Stirring at room temperature (25 to 30° C.) produced two clear phases; the lower aqueous phase appears bright yellow. The mixture was cooled to 0° C. whereupon some of the dissolved salts precipitated. One mmol of olefin was added at once, and the heterogeneous slurry was stirred vigorously at 0° C. for 6-24 h (progress was monitored by TLC). While the mixture was stirred at 0° C., solid anhydrous sodium sulfite (1.5 g) was added and the mixture was allowed to warm to room temperature (rt) and stirred for 30-60 min. Ethyl acetate or methylene chloride (10 mL) was added to the reaction mixture, and after separation of the layers, the aqueous phase was further extracted with the organic solvent (3×5 mL). The combined organic extracts were dried over anhydrous magnesium sulfate and concentrated to give the diol and the ligand. This crude product was purified by flash chromatography (silica gel, EtOAc/hexanes; the ligand does not move in this solvent system) to afford the 1,2-diol compound of formula C in 80-98% yield.

c) General Procedure for Monotosylation of 1,2-Diol:

To a stirred solution of diol (1.0 eq) in dichloromethane was added pyridine (10.0 eq) at 0° C. followed by para-toluenesulfonyl chloride (2.0 eq) and reaction mixture was stirred for 3-4 h at 0° C. After the completion of reaction (by TLC), reaction mixture was treated with 10% HCl at 0° C., and extracted with ethyl acetate. The extract was washed with water (2×20 mL) and brine (1×20 mL), dried over anhydrous $Na_2SO_4$, filtered, and concentrated. The concentrate was purified by flash chromatography on silica gel to give the desired compound of formula D.

d) General Procedure for Preparation of 1,2-Azido Alcohol:

A solution of monotosylate (1.0 eq), tetrabutylammonium iodide (0.05 eq) and sodium azide (3.0 eq) in DMF was heated at 80-90° C. for 3-4 h. After the completion of reaction, reaction mixture was cooled to 0° C. and added water and brine. The aqueous layer was extracted with ethyl acetate (3×35 mL). The combined organic layers were washed with brine (2×20 mL), dried over anhydrous $Na_2SO_4$, filtered, and concentrated. The concentrate was purified by flash chromatography on silica gel to give the desired compound of formula E.

e) General Procedure for Preparation of 1,2-Aminoalcohol:

1,2-Azido alcohol was dissolved in anhydrous MeOH and 10% palladium on carbon (10% w/w) was added. The reaction mixture was stirred under hydrogen atmosphere until completion as determined by TLC and disappearance of azide spot. The hydrogen was carefully released, and the reaction mixture was filtered through celite (pre-washed with MeOH). Solvent removal in vacuo gave the crude compound of formula F that was used in the next step without further purification.

f) General Procedure for Coupling with DCC/DMAP:

To a stirred solution of 1,2-diol compound of formula C/1,2-amino alcohol compound of formula F (1 mmol) in dry $CH_2Cl_2$ (5 mL), cinnamic acid (2.5 mmol), DCC (2.5 mmol) and DMAP (4.0 mmol) were added and stirred at room temperature for 12 h. Then the reaction mixture was treated with $H_2O$ (2 mL) and extracted with $CH_2Cl_2$ (2×20 mL). The combined organic layers were washed with water (10 mL), brine (10 mL), dried over anhydrous $Na_2SO_4$ and concentrated to give a crude residue, which was purified by column chromatography (100-200 silica gel, 1:1 EtOAc/n-hexane) to afford final compound of formula I in 75-80% yield.

Example 1: (S)-2-cinnamamido-1-(3,4-dimethoxyphenyl)ethyl cinnamate (1)

Colorless solid; mp 132-135° C.; $R_f$=0.34 (EtOAc/P.E. 2:3 v/v); $[\alpha]_D^{26}$+41.5 (c 1, $CHCl_3$); IR ($CHCl_3$): 3364, 3301, 3068, 3017, 2932, 2846, 1710, 1664, 1627, 1516, 1455, 1336, 1258, 1217, 1163, 1030, 984, 861, 758, 672; $^1$H NMR (400 MHz, $CDCl_3$) δ 7.72 (d, J=16.14 Hz, 1H), 7.63 (d, J=15.65 Hz, 1H), 7.43-7.55 (m, 4H), 7.29-7.42 (m, 6H), 6.91-7.03 (m, 2H), 6.86 (d, J=8.07 Hz, 1H), 6.49 (d, J=16.14 Hz, 1H), 6.39 (d, J=15.65 Hz, 1H), 6.07 (brs, 1H), 6.01 (dd, J=5.01, 7.70 Hz, 1H), 3.89 (s, 3H), 3.86 (s, 3H), 3.83-3.92 (m, 2H, overlapped); $^{13}$C NMR (100 MHz, $CDCl_3$) δ 166.5, 165.9, 149.2, 149.1, 145.8, 141.5, 134.7, 134.1, 130.5, 130.2, 129.7, 128.9, 128.7, 128.1, 127.8, 120.3, 119.0, 117.6, 111.2, 109.8, 74.7, 55.9, 55.9, 44.6; ESI-LCMS: m/z (M+Na)$^+$ 479.95; HRMS: m/z for $C_{28}H_{27}NO_5Na$ ([M+Na]$^+$): calcd 480.1781, found 480.1772.

Example 2: (R)-2-cinnamamido-1-(3,4-dimethoxyphenyl)ethyl cinnamate (2)

Colorless solid; mp 123-125° C.; $R_f$=0.34 (EtOAc/P.E. 2:3 v/v); $[\alpha]_D^{23}$-42.0 (c 1, $CHCl_3$); IR ($CHCl_3$): 3364, 3301, 3068, 3017, 2932, 2846, 1710, 1664, 1627, 1516, 1455, 1336, 1258, 1217, 1163, 1030, 984, 861, 758, 672; $^1$H NMR (200 MHz, $CDCl_3$) δ 7.57-7.80 (m, 2H), 7.28-7.56 (m, 10H), 6.82-7.06 (m, 3H), 6.32-6.58 (m, 2H), 5.94-6.15 (m, 2H), 3.90 (s, 3H), 3.87 (s, 3H), 3.80-3.97 (m, 2H, overlapped); $^{13}$C NMR (100 MHz, $CDCl_3$) δ 166.5, 165.9, 149.2, 149.1, 145.8, 141.5, 134.7, 134.1, 130.5, 130.2, 129.7, 128.9, 128.7, 128.1, 127.8, 120.3, 119.0, 117.6, 111.2, 109.8, 74.7, 55.9, 55.9, 44.6; ESI-LCMS: m/z (M+Na)$^+$ 480.25; HRMS: m/z 480.1770 (calcd for $C_{28}H_{27}NO_5Na$, [M+Na]$^+$, 480.1781).

Example 3: (S)-1-(3,4-dimethoxyphenyl)ethane-1,2-diyl(2E,2'E)-bis(3-phenyl acrylate)(3)

Colorless viscous liquid; $R_f$=0.48, EtOAc/P.E. 3:7 v/v; $[\alpha]_D^{24}$+29.4 (c 0.5, $CHCl_3$); IR ($CHCl_3$): 3021, 2961, 2938, 1713, 1637, 1579, 1519, 1451, 1422, 1330, 1310, 1256, 1216, 1161, 1071, 1028, 863, 756, 711, 684; $^1$H NMR (200 MHz, $CDCl_3$) δ 7.76 (d, J=6.82 Hz, 1H), 7.68 (d, J=6.69 Hz, 1H), 7.44-7.59 (m, 4H), 7.31-7.44 (m, 6H), 6.84-7.09 (m, 3H), 6.39-6.59 (m, 2H), 6.19 (dd, J=3.98, 8.15 Hz, 1H), 4.42-4.67 (m, 2H), 3.91 (s, 3H), 3.88 (s, 3H); $^{13}$C NMR (50 MHz, $CDCl_3$) δ 166.6, 166.1, 149.3, 149.1, 145.5, 145.5, 134.2, 130.4, 129.1, 128.9, 128.1, 119.4, 117.7, 117.5, 73.4, 66.1, 56.0, 55.9; ESI-LCMS: m/z (M+Na)$^+$ 481.02; HRMS: m/z for $C_{28}H_{26}O_6Na$ ([M+Na]$^+$): calcd 481.1622, found 481.1626.

Example 4: (R)-1-(3,4-dimethoxyphenyl)ethane-1,2-diyl (2E,2'E)-bis(3-phenyl acrylate) (4)

Colorless viscous liquid; $R_f$=0.48, EtOAc/P.E. 3:7 v/v; $[\alpha]_D^{25}$-26.9 (c 0.5, $CHCl_3$); IR ($CHCl_3$): 3364, 3020, 1712, 1664, 1637, 1518, 1464, 1450, 1421, 1388, 1329, 1310, 1216, 1161, 1027, 988, 928, 864, 771, 668; $^1$H NMR (200 MHz, $CDCl_3$) δ 7.76 (d, J=6.57 Hz, 1H), 7.68 (d, J=6.57 Hz, 1H), 7.44-7.60 (m, 4H), 7.31-7.44 (m, 6H), 6.83-7.09 (m, 3H), 6.37-6.59 (m, 2H), 6.18 (dd, J=3.92, 8.21 Hz, 1H), 4.42-4.67 (m, 2H), 3.88 (s, 3H), 3.91 (s, 3H); $^{13}$C NMR (50 MHz, $CDCl_3$) δ 166.6, 166.1, 149.3, 149.1, 145.6, 145.6, 134.3, 134.3, 130.5, 128.9, 128.2, 119.4, 117.8, 117.5, 111.2, 73.5, 66.2, 56.0, 56.0; ESI-LCMS: m/z (M+Na)$^+$ 481.02; HRMS: m/z for $C_{28}H_{26}O_6Na$ ([M+Na]$^+$): calcd 481.1622, found 481.1626.

Example 5: (S)-2-cinnamamido-1-(3,4,5-trimethoxyphenyl)ethyl cinnamate (5)

Colorless solid; mp 126-128° C.; $R_f$=0.37, EtOAc/P.E. 2:3 v/v; $[\alpha]_D^{26}$+39 (c 1, $CHCl_3$); IR ($CHCl_3$): 3361, 3165, 3018, 1711, 1664, 1633, 1594, 1509, 1463, 1422, 1330, 1216, 1164, 1130, 770, 668; $^1$H NMR (200 MHz, $CDCl_3$) δ 7.59-7.81 (m, 2H), 7.44-7.57 (m, 4H), 7.30-7.44 (m, 6H), 6.65 (s, 2H), 6.34-6.58 (m, 2H), 5.92-6.10 (m, 2H), 3.87 (s, 6H), 3.84 (s, 3H), 3.82-3.90 (m, 2H, overlapped); $^{13}$C NMR (100 MHz, CDCl₃) δ 166.6, 166.0, 153.4, 149.2, 149.1, 145.8, 141.5, 134.7, 134.1, 130.5, 130.2, 129.7, 128.9, 128.8, 128.2, 127.8, 120.3, 119.0, 117.5, 111.1, 109.8, 103.5, 74.7, 60.8, 55.9, 55.9, 44.6; ESI-LCMS: m/z (M+Na)⁺ 510.26; HRMS: m/z for C₂₉H₂₉NO₆Na ([M+Na]⁺): calcd 510.1887, found 510.1876.

Example 6: (R)-2-cinnamamido-1-(3,4,5-trimethoxyphenyl)ethyl cinnamate (6)

Colorless solid; mp 126-127° C.; $R_f$=0.37, EtOAc/P.E. 2:3 v/v; $[\alpha]_D^{26}$−39 (c 1, CHCl₃); IR (CHCl₃): 3361, 3165, 3018, 1711, 1664, 1633, 1594, 1509, 1463, 1422, 1330, 1216, 1164, 1130, 770, 668; ¹H NMR (200 MHz, CDCl₃) 7.59-7.81 (m, 2H), 7.44-7.57 (m, 4H), 7.30-7.44 (m, 6H), 6.65 (s, 2H), 6.34-6.58 (m, 2H), 5.92-6.10 (m, 2H), 3.87 (s, 6H), 3.84 (s, 3H), 3.82-3.90 (m, 2H, overlapped); ¹³C NMR (100 MHz, CDCl₃) δ 166.6, 166.0, 153.4, 149.2, 149.1, 145.8, 141.5, 134.7, 134.1, 130.5, 130.2, 129.7, 128.9, 128.8, 128.2, 127.8, 120.3, 119.0, 117.5, 111.1, 109.8, 103.5, 74.7, 60.8, 55.9, 55.9, 44.6; ESI-LCMS: m/z (M+Na)⁺ 510.08; HRMS: m/z for C₂₉H₂₉NO₆Na ([M+Na]⁺): calcd 510.1887, found 510.1873.

Example 7: (S)-1-(3,4,5-trimethoxyphenyl)ethane-1,2-diyl(2E,2'E)-bis(3-phenyl acrylate) (7)

Colorless viscous liquid; $R_f$=0.45, EtOAc/P.E. 3:7 v/v; $[\alpha]_D^{28}$+23 (c1, CHCl₃); IR (CHCl₃): 3019, 2956, 2921, 1713, 1636, 1593, 1503, 1458, 1377, 1311, 1213, 1158, 1129, 982, 751, 669; ¹H NMR (400 MHz, CDCl₃) δ 7.67-7.79 (m, 2H), 7.48-7.57 (m, 4H), 7.34-7.44 (m, 6H), 6.68 (s, 2H), 6.42-6.58 (m, 2H), 6.16 (dd, J=3.55, 8.44 Hz, 1H), 4.46-4.62 (m, 2H), 3.89 (s, 6H), 3.84 (s, 3H); ¹³C NMR (100 MHz, CDCl₃) δ 166.6, 160.0, 153.4, 145.8, 145.6, 138.1, 134.2, 132.2, 130.5, 130.5, 128.9, 128.1, 117.5, 117.4, 103.8, 73.7, 66.2, 60.8, 56.2; ESI-LCMS: m/z (M+Na)⁺ 511.04; HRMS: m/z for C₂₉H₂₈O₇Na ([M+Na]⁺): calcd 511.1727, found 511.1736.

Example 8: (R)-1-(3,4,5-trimethoxyphenyl)ethane-1,2-diyl(2E,2'E)-bis(3-phenyl acrylate) (8)

Colorless viscous liquid; $R_f$=0.45, EtOAc/P.E. 3:7 v/v; $[\alpha]_D^{25}$−22.4 (c 0.5, CHCl₃); IR (CHCl₃): 3360, 3164, 3020, 2935, 2848, 1713, 1635, 1603, 1509, 1458, 1419, 1319, 1216, 1164, 866, 762, 669; ¹H NMR (500 MHz, CDCl₃) δ 7.68-7.78 (m, 2H), 7.48-7.57 (m, 4H), 7.35-7.42 (m, 6H), 6.68 (s, 2H), 6.54 (d, J=15.87 Hz, 1H), 6.45 (d, J=15.87 Hz, 1H), 6.16 (dd, J=3.36, 8.55 Hz, 1H), 4.57 (dd, J=8.54, 11.90 Hz, 1H), 4.49 (dd, J=3.51, 12.05 Hz, 1H), 3.89 (s, 6H), 3.84 (s, 3H); ¹³C NMR (125 MHz, CDCl₃) δ 166.6, 166.0, 153.4, 145.8, 145.6, 138.2, 134.2, 132.2, 130.5, 130.5, 128.9, 128.2, 128.1, 117.5, 117.4, 103.8, 73.7, 66.2, 60.8, 56.2; ESI-LCMS: m/z (M+Na)⁺511.06; HRMS: m/z for C₂₉H₂₈O₇Na ([M+Na]⁺): calcd 511.1727, found 511.1733.

Example 9: (S)-2-cinnamamido-1-(2-methoxyphenyl)ethyl cinnamate (9)

Colorless solid; mp 112-114° C.; $[\alpha]_D^{27}$+31.5 (c 0.5, CHCl₃); $R_f$=0.45, EtOAc/P.E. 2:3 v/v; IR (CHCl₃): 3369, 3016, 2925, 2856, 2404, 1710, 1666, 1629, 1526, 1455, 1323, 1215, 1170, 1040, 982, 859, 764, 673; ¹H NMR (400 MHz, CDCl₃) δ 7.74 (d, J=16.14 Hz, 1H), 7.59 (d, J=15.65 Hz, 1H), 7.26-7.55 (m, 12H), 6.88-7.02 (m, 2H), 6.55 (d, J=16.14 Hz, 1H), 6.42-6.49 (dd, J=3.42, 7.83 Hz, 1H), 6.40 (d, J=15.65, 1H), 6.15 (brs, 1H), 3.88 (s, 3H), 3.77-3.97 (m, 2H, overlapped); ¹³C NMR (100 MHz, CDCl₃) δ 166.5, 165.9, 156.2, 145.7, 141.0, 134.8, 134.2, 130.4, 129.6, 129.4, 128.9, 128.7, 128.2, 127.8, 126.4, 126.1, 120.7, 120.6, 117.7, 110.7, 69.9, 55.5, 43.9; ESI-LCMS: m/z (M+Na)⁺ 450.13; HRMS: m/z for C₂₇H₂₅NO₄Na ([M+Na]⁺): calcd 450.1676, found 450.1668.

Example 10: (R)-2-cinnamamido-1-(2-methoxyphenyl)ethyl cinnamate (10)

Colorless solid; mp 112-114° C.; $[\alpha]_D^{27}$−28.7 (c 0.5, CHCl₃); $R_f$=0.45, EtOAc/P.E. 2:3 v/v; IR (CHCl₃): 3369, 3016, 2925, 2856, 2404, 1710, 1666, 1629, 1526, 1455, 1323, 1215, 1170, 1040, 982, 859, 764, 673; ¹H NMR (400 MHz, CDCl₃) δ 7.74 (d, J=16.14 Hz, 1H), 7.59 (d, J=15.65 Hz, 1H), 7.25-7.55 (m, 12H), 6.87-7.03 (m, 2H), 6.52 (d, J=16.14 Hz, 1H), 6.44-6.47 (dd, J=3.67, 8.07 Hz, 1H), 6.38 (d, J=15.65 Hz, 1H), 6.17 (brs, 1H), 3.88 (s, 3H), 3.77-3.98 (m, 2H, overlapped); ¹³C NMR (100 MHz, CDCl₃) δ 166.5, 165.9, 156.2, 145.7, 141.0, 134.8, 134.2, 130.4, 129.6, 129.4, 128.9, 128.7, 128.2, 127.8, 126.4, 126.1, 120.7, 120.6, 117.7, 110.7, 69.9, 55.5, 43.9; ESI-LCMS: m/z (M+Na)⁺ 450.12; HRMS: m/z for C₂₇H₂₅NO₄Na ([M+Na]⁺): calcd 450.1676, found 450.1673.

Example 11: (S)-1-(2-methoxyphenyl)ethane-1,2-diyl (2E,2'E)-bis(3-phenylacrylate) (11)

Colorless viscous liquid; $R_f$=0.44, EtOAc/P.E. 1:4 v/v; $[\alpha]_D^{28}$+0.8 (c 1, CHCl₃); IR (CHCl₃): 2956, 2919, 1713, 1635, 1600, 1493, 1455, 1355, 1308, 1278, 1245, 1157, 1048, 1024, 981, 863, 758, 709, 683; ¹H NMR (200 MHz, CDCl₃) δ 7.61-7.83 (m, 2H), 7.29-7.60 (m, 12H), 6.87-7.04 (m, 2H), 6.38-6.67 (m, 3H), 4.47-4.58 (m, 2H), 3.89 (s, 3H); ¹³C NMR (50 MHz, CDCl₃) δ 166.6, 165.9, 156.3, 145.4, 145.2, 134.4, 130.3, 130.3, 129.4, 128.8, 128.1, 128.1, 126.9, 125.0, 120.6, 118.0, 117.8, 110.6, 68.9, 65.4, 55.5; ESI-LCMS: m/z (M+Na)⁺ 451.04; HRMS: m/z for C₂₇H₂₄O₅Na ([M+Na]⁺): calcd 451.1516, found 451.1507.

Example 12: (R)-1-(2-methoxyphenyl)ethane-1,2-diyl (2E,2'E)-bis(3-phenylacrylate) (12)

Colorless viscous liquid; $R_f$=0.44, EtOAc/P.E. 1:4 v/v; $[\alpha]_D^{28}$−0.8 (c 1, CHCl₃); IR (CHCl₃): 3019, 2360, 2341, 1713, 1663, 1579, 1495, 1439, 1329, 1310, 1283, 1248, 1216, 1162, 1050, 980, 770, 711, 684; ¹H NMR (200 MHz, CDCl₃) δ 7.62-7.83 (m, 2H), 7.29-7.60 (m, 12H), 6.87-7.05 (m, 2H), 6.38-6.66 (m, 3H), 4.48-4.57 (m, 2H), 3.89 (s, 3H); ¹³C NMR (100 MHz, CDCl₃) δ 166.7, 166.0, 156.3, 145.4, 145.2, 134.4, 130.4, 130.4, 129.5, 128.9, 128.9, 128.2, 128.2, 127.0, 125.0, 120.7, 118.0, 117.8, 110.6, 69.0, 65.4, 55.6; ESI-LCMS: m/z (M+Na)⁺ 451.10; HRMS: m/z for C₂₇H₂₄O₅Na ([M+Na]⁺): calcd 451.1516, found 451.1514.

Example 13: (S)-2-cinnamamido-1-(3-methoxyphenyl)ethyl cinnamate (13)

Colorless solid; mp 139-141° C.; $R_f$=0.39, EtOAc/P.E. 2:3 v/v; $[\alpha]_D^{23}$+42.5 (c 0.5, CHCl₃); IR (CHCl₃): 3361, 3164, 3019, 2400, 1710, 1664, 1634, 1514, 1450, 1411, 1389, 1330, 1311, 1215, 1165, 1129, 1043, 978, 769, 668; ¹H NMR (500 MHz, CDCl₃) δ 7.73 (d, J=15.87 Hz, 1H), 7.63 (d, J=15.56 Hz, 1H), 7.42-7.55 (m, 4H), 7.26-7.41 (m, 7H), 6.92-7.05 (m, 2H), 6.86 (d, J=7.93 Hz, 1H), 6.50 (d, J=16.17 Hz, 1H), 6.39 (d, J=15.56 Hz, 1H), 6.14 (brs, 1H), 6.03 (dd, J=3.51, 8.09 Hz, 1H), 3.80 (s, 3H), 3.78-3.94 (m, 2H, overlapped); $^{13}$C NMR (125 MHz, CDCl$_3$) δ 166.4, 166.0, 159.8, 145.9, 141.5, 139.3, 134.7, 134.1, 130.5, 129.8, 129.7, 128.9, 128.8, 128.2, 127.8, 120.3, 118.6, 117.5, 113.9, 112.1, 74.7, 55.3, 44.8; ESI-LCMS: m/z (M+Na)$^+$ 450.02; HRMS: m/z for C$_{27}$H$_{25}$NO$_4$Na ([M+Na]$^+$): calcd 450.1676, found 450.1673.

Example 14: (R)-2-cinnamamido-1-(3-methoxyphenyl)ethyl cinnamate (14)

Colorless solid; mp 138-140° C.; R$_f$=0.39, EtOAc/P.E. 2:3 v/v; [α]$_D^{23}$ −47.8 (c 0.5, CHCl$_3$); IR (CHCl$_3$): 3361, 3164, 3019, 2400, 1710, 1664, 1634, 1514, 1450, 1411, 1389, 1330, 1311, 1215, 1165, 1129, 1043, 978, 769, 668; $^1$H NMR (200 MHz, CDCl$_3$) δ 7.57-7.79 (m, 2H), 7.43-7.55 (m, 4H), 7.28-7.42 (m, 7H), 6.95-7.05 (m, 2H), 6.86 (ddd, J=0.88, 2.56, 8.18 Hz, 1H), 6.33-6.56 (m, 2H), 5.98-6.13 (m, 2H), 3.81 (s, 3H), 3.99-3.73 (m, 2H, overlapped); $^{13}$C NMR (50 MHz, CDCl$_3$) δ 166.3, 165.9, 159.8, 145.9, 141.5, 139.4, 134.7, 134.2, 130.5, 129.8, 129.7, 128.9, 128.8, 128.2, 127.8, 120.3, 118.7, 117.5, 113.9, 112.2, 74.7, 55.3, 44.8; ESI-LCMS: m/z (M+Na)$^+$ 450.04; HRMS: m/z for C$_{27}$H$_{25}$NO$_4$Na ([M+Na]$^+$): calcd 450.1676, found 450.1671.

Example 15: (S)-1-(3-methoxyphenyl)ethane-1,2-diyl (2E,2'E)-bis(3-phenylacrylate) (15)

Colorless solid; mp 67-69° C.; R$_f$=0.45, EtOAc/P.E. 1:4 v/v; [α]$_D^{23}$ +22.7 (c 0.5, CHCl$_3$); IR (CHCl$_3$): 3365, 3169, 3021, 2931, 1713, 1633, 1451, 1316, 1268, 1216, 1165, 1042, 986, 865, 765, 668; $^1$H NMR (200 MHz, CDCl$_3$) δ 7.68 (d, J=9.47 Hz, 1H), 7.76 (d, J=9.47 Hz, 1H), 7.45-7.58 (m, 4H), 7.26-7.44 (m, 7H), 6.98-7.09 (m, 2H), 6.88 (ddd, J=0.88, 2.53, 8.21 Hz, 1H), 6.38-6.59 (m, 2H), 6.21 (dd, J=4.67, 7.20 Hz, 1H), 4.46-4.63 (m, 2H), 3.82 (s, 3H); $^{13}$C NMR (50 MHz, CDCl$_3$) δ 166.5, 165.9, 159.8, 145.6, 145.5, 138.2, 134.3, 130.4, 129.8, 128.9, 128.2, 119.0, 117.7, 117.5, 114.0, 112.5, 73.5, 66.2, 55.3; ESI-LCMS: m/z (M+Na)$^+$ 451.00; HRMS: m/z for C$_{27}$H$_{24}$O$_5$Na ([M+Na]$^+$): calcd 451.1516, found 451.1513.

Example 16: (R)-1-(3-methoxyphenyl)ethane-1,2-diyl (2E,2'E)-bis(3-phenylacrylate) (16)

Colorless solid; mp 67-69° C.; R$_f$=0.45, EtOAc/P.E. 1:4 v/v; [α]$_D^{23}$ −25.6 (c 0.5, CHCl$_3$); IR (CHCl$_3$): 3365, 3169, 3021, 2931, 1713, 1633, 1451, 1316, 1268, 1216, 1165, 1042, 986, 865, 765, 668; $^1$H NMR (200 MHz, CDCl$_3$) δ 7.68 (d, J=9.47 Hz, 1H), 7.76 (d, J=9.47 Hz, 1H), 7.46-7.58 (m, 4H), 7.26-7.43 (m, 7H), 6.97-7.09 (m, 2H), 6.88 (ddd, J=0.88, 2.53, 8.21 Hz, 1H), 6.38-6.59 (m, 2H), 6.21 (dd, J=4.61, 7.26 Hz, 1H), 4.47-4.63 (m, 2H), 3.82 (s, 3H); $^{13}$C NMR (50 MHz, CDCl$_3$) δ 166.5, 165.9, 159.8, 145.6, 145.5, 138.2, 134.3, 130.4, 129.8, 128.9, 128.2, 119.0, 117.7, 117.5, 114.0, 112.5, 73.5, 66.2, 55.3; ESI-LCMS: m/z (M+Na)$^+$ 451.01; HRMS: m/z for C$_{27}$H$_{24}$O$_5$Na ([M+Na]$^+$): calcd 451.1516, found 451.1513.

Example 17: (S)-2-cinnamamido-1-(4-methoxyphenyl)ethyl cinnamate (17)

Colorless solid; mp 137-139° C.; R$_f$=0.38, EtOAc/P.E. 2:3 v/v; [α]$_D^{26}$ +51.5 (c 0.6, CHCl$_3$); IR (CHCl$_3$): 3361, 3165, 3019, 1688, 1620, 1525, 1411, 1390, 1216, 1043, 771, 669; $^1$H NMR (200 MHz, CDCl$_3$) δ 7.57-7.77 (m, 2H), 7.42-7.54 (m, 4H), 7.28-7.41 (m, 8H), 6.85-6.95 (m, 2H), 6.32-6.54 (m, 2H), 6.06-6.16 (m, 1H), 6.01 (dd, J=5.56, 7.33 Hz, 1H), 3.81-3.92 (m, 2H), 3.79 (s, 3H); $^{13}$C NMR (50 MHz, CDCl$_3$) δ 166.5, 165.9, 159.7, 145.7, 141.4, 134.7, 134.2, 130.4, 129.8, 129.7, 128.9, 128.7, 128.1, 128.0, 127.8, 120.4, 117.5, 114.1, 74.7, 55.3, 44.6; ESI-LCMS: m/z (M+Na)$^+$ 449.96; HRMS: m/z for C$_{27}$H$_{25}$NO$_4$Na ([M+Na]$^+$): calcd 450.1676, found 450.1673.

Example 18: (R)-2-cinnamamido-1-(4-methoxyphenyl)ethyl cinnamate (18)

Colorless solid; mp 138-140° C.; R$_f$=0.38, EtOAc/P.E. 2:3 v/v; [α]$_D^{26}$ −59.5 (c 0.58, CHCl$_3$); IR (CHCl$_3$): 3361, 3165, 3019, 1688, 1620, 1525, 1411, 1390, 1216, 1043, 771, 669; $^1$H NMR (200 MHz, CDCl$_3$) δ 7.57-7.78 (m, 2H), 7.42-7.54 (m, 4H), 7.28-7.42 (m, 8H), 6.85-6.96 (m, 2H), 6.32-6.55 (m, 2H), 6.13 (t, J=5.49 Hz, 1H), 6.01 (dd, J=5.31, 7.58 Hz, 1H), 3.81-3.93 (m, 2H), 3.79 (s, 3H); $^{13}$C NMR (50 MHz, CDCl$_3$) δ 166.5, 165.9, 159.7, 145.7, 141.4, 134.7, 134.2, 130.4, 129.8, 129.7, 128.9, 128.7, 128.1, 128.0, 127.8, 120.4, 117.5, 114.1, 74.7, 55.3, 44.6; ESI-LCMS: m/z (M+Na)$^+$ 450.31; HRMS: m/z for C$_{27}$H$_{25}$NO$_4$Na ([M+Na]$^+$): calcd 450.1676, found 450.1671.

Example 19: (S)-1-(4-methoxyphenyl)ethane-1,2-diyl (2E,2'E)-bis(3-phenylacrylate) (19)

Colorless solid; mp 93-96° C.; R$_f$=0.43, EtOAc/P.E. 1:4 v/v; [α]$_D^{26}$ +32.5 (c 0.5, CHCl$_3$); IR (CHCl$_3$): 3022, 2964, 2358, 1713, 1633, 1513, 1452, 1251, 1215, 1167, 1036, 986, 930, 896, 832, 762, 672, 607; $^1$H NMR (500 MHz, CDCl$_3$) δ 7.66-7.76 (m, 2H), 7.47-7.56 (m, 4H), 7.33-7.43 (m, 8H), 6.92 (d, J=8.85 Hz, 2H), 6.41-6.54 (m, 2H), 6.19 (dd, J=3.51, 8.39 Hz, 1H), 4.57 (dd, J=8.54, 11.90 Hz, 1H), 4.48 (dd, J=3.66, 11.90 Hz, 1H), 3.80 (s, 3H); $^{13}$C NMR (125 MHz, CDCl$_3$) δ 166.6, 166.1, 159.8, 145.5, 134.3, 130.4, 128.9, 128.2, 117.8, 117.5, 114.1, 73.2, 66.1, 55.3; ESI-LCMS: m/z (M+Na)$^+$ 451.07; HRMS: m/z for C$_{27}$H$_{24}$O$_5$Na ([M+Na]$^+$): calcd 451.1516, found 451.1514.

Example 20: (R)-1-(4-methoxyphenyl)ethane-1,2-diyl (2E,2'E)-bis(3-phenylacrylate) (20)

Colorless solid; mp 76-79° C.; R$_f$=0.43, EtOAc/P.E. 1:4 v/v; [α]$_D^{26}$ −31.3 (c 0.5, CHCl$_3$); IR (CHCl$_3$): 3022, 2964, 2358, 1713, 1633, 1513, 1452, 1251, 1215, 1167, 1036, 986, 930, 896, 832, 762, 672, 607; $^1$H NMR (400 MHz, CDCl$_3$) δ 7.65-7.77 (m, 2H), 7.46-7.57 (m, 4H), 7.33-7.44 (m, 8H), 6.92 (d, J=8.80 Hz, 2H), 6.40-6.55 (m, 2H), 6.19 (dd, J=3.79, 8.44 Hz, 1H), 4.44-4.61 (m, 2H), 3.80 (s, 3H); $^{13}$C NMR (100 MHz, CDCl$_3$) δ 166.6, 166.0, 159.8, 145.4, 134.3, 134.2, 130.4, 128.9, 128.7, 128.2, 128.1, 117.8, 117.5, 114.1, 73.2, 66.1, 55.3; ESI-LCMS: m/z (M+Na)$^+$ 451.09; HRMS: m/z for C$_{27}$H$_{24}$O$_5$Na ([M+Na]$^+$): calcd 451.1516, found 451.1514.

Example 21: (S)-2-cinnamamido-1-(2,3-dimethoxyphenyl)ethyl cinnamate (21)

Colorless solid; mp 105-108° C.; R$_f$=0.38, EtOAc/P.E. 2:3 v/v; [α]$_D^{26}$ −7.9 (c 0.5, CHCl$_3$); IR (CHCl$_3$): 3366, 3170, 3020, 2358, 1706, 1666, 1627, 1520, 1419, 1216, 1168, 1040, 927, 769, 763, 668; $^1$H NMR (200 MHz, CDCl$_3$) δ 7.56-7.80 (m, 2H), 7.43-7.56 (m, 4H), 7.29-7.42 (m, 6H), 6.99-7.15 (m, 2H), 6.90 (dd, 1H, J1=7.58, J2=2.15), 6.32-6.58 (m, 3H), 6.14 (t, J=5.31 Hz, 1H), 3.98 (s, 3H), 3.87 (s, 3H), 3.90-3.84 (m, 2H, overlapped); $^{13}$C NMR (50 MHz, CDCl$_3$) δ 166.5, 166.0, 152.6, 146.2, 145.8, 141.3, 134.8, 134.2, 131.9, 130.5, 129.7, 128.9, 128.8, 128.2, 127.9, 124.6, 120.5, 118.4, 117.6, 112.4, 69.9, 60.9, 55.8, 44.3; ESI-LCMS: m/z (M+Na)$^+$480.22; HRMS: m/z for C$_{28}$H$_{27}$NO$_5$Na ([M+Na]$^+$): calcd 480.1781, found 480.1777.

Example 22: (R)-2-cinnamamido-1-(2,3-dimethoxyphenyl)ethyl cinnamate (22)

Colorless solid; mp 105-107° C.; R$_f$=0.38, EtOAc/P.E. 2:3 v/v; [α]$_D$$^{26}$+8.0 (c 0.58, CHCl$_3$); IR (CHCl$_3$): 3366, 3170, 3020, 2358, 1706, 1666, 1627, 1520, 1419, 1216, 1168, 1040, 927, 763, 668; $^1$H NMR (200 MHz, CDCl$_3$) δ 7.56-7.80 (m, 2H), 7.43-7.56 (m, 4H), 7.29-7.42 (m, 6H), 6.99-7.15 (m, 2H), 6.90 (dd, 1H, J1=7.58, J2=2.15), 6.32-6.58 (m, 3H), 6.14 (t, J=5.31 Hz, 1H), 3.98 (s, 3H), 3.87 (s, 3H), 3.90-3.84 (m, 2H, overlapped); $^{13}$C NMR (50 MHz, CDCl$_3$) δ 166.5, 166.0, 152.6, 146.2, 145.8, 141.3, 134.8, 134.2, 131.9, 130.5, 129.7, 128.9, 128.8, 128.2, 127.9, 124.6, 120.5, 118.4, 117.6, 112.4, 69.9, 60.9, 55.8, 44.3; ESI-LCMS: m/z (M+Na)$^+$480.23; HRMS: m/z for C$_{28}$H$_{27}$NO$_5$Na ([M+Na]$^+$): calcd 480.1781, found 480.1780.

Example 23: (S)-1-(2,3-dimethoxyphenyl)ethane-1,2-diyl (2E,2'E)-bis(3-phenyl acrylate) (23)

Colorless viscous liquid; R$_f$=0.4, EtOAc/P.E. 1:4 v/v; [α]$_D$$^{23}$−17.0 (c 0.5, CHCl$_3$); IR (CHCl$_3$): 3021, 2943, 2843, 2358, 1713, 1637, 1482, 1448, 1298, 1272, 1215, 1168, 1084, 1042, 993, 929, 868, 760, 672, 611; $^1$H NMR (500 MHz, CDCl$_3$) δ 7.65-7.78 (m, 2H), 7.52 (m, 4H), 7.32-7.42 (m, 6H), 7.01-7.12 (m, 2H), 6.90 (d, J=7.63 Hz, 1H), 6.49-6.60 (m, 2H), 6.45 (d, J=16.17 Hz, 1H), 4.59 (dd, J=8.39, 11.75 Hz, 1H), 4.46 (dd, J=3.05, 11.60 Hz, 1H), 4.00 (s, 3H), 3.87 (s, 3H); $^{13}$C NMR (125 MHz, CDCl$_3$) δ 166.6, 166.0, 152.6, 146.4, 145.4, 145.3, 134.3, 134.3, 130.5, 130.4, 130.3, 128.9, 128.8, 128.1, 124.2, 118.8, 117.8, 117.7, 112.6, 69.1, 65.6, 60.8, 55.8; ESI-LCMS: m/z (M+Na)$^+$ 481.04; HRMS: m/z for C$_{28}$H$_{26}$O$_6$Na ([M+Na]$^+$): calcd 481.1622, found 481.1616.

Example 24: (R)-1-(2,3-dimethoxyphenyl)ethane-1,2-diyl(2E,2'E)-bis(3-phenyl acrylate) (24)

Colorless viscous liquid; R$_f$=0.4, EtOAc/P.E. 1:4 v/v; [α]$_D$$^{23}$+18.0 (c 0.5, CHCl$_3$); IR (CHCl$_3$): 3021, 2943, 2843, 2358, 1713, 1637, 1482, 1448, 1298, 1272, 1215, 1168, 1084, 1042, 993, 929, 868, 760, 672, 611; $^1$H NMR (500 MHz, CDCl$_3$) δ 7.65-7.77 (m, 2H), 7.47-7.57 (m, 4H), 7.32-7.41 (m, 6H), 7.01-7.11 (m, 2H), 6.90 (d, J=7.63 Hz, 1H), 6.49-6.60 (m, 2H), 6.45 (d, J=16.17 Hz, 1H), 4.59 (dd, J=8.24, 11.90 Hz, 1H), 4.46 (dd, J=3.05, 11.90 Hz, 1H), 4.00 (s, 3H), 3.87 (s, 3H); $^{13}$C NMR (125 MHz, CDCl$_3$) δ 166.6, 166.0, 152.6, 146.4, 145.5, 145.3, 134.3, 134.3, 130.5, 130.4, 130.3, 128.9, 128.8, 128.2, 124.2, 118.8, 117.8, 117.7, 112.5, 69.1, 65.6, 60.8, 55.8; ESI-LCMS: m/z (M+Na)$^+$ 481.09; HRMS: m/z for C$_{28}$H$_{26}$O$_6$Na ([M+Na]$^+$): calcd 481.1622, found 481.1619.

Example 25: (S)-2-cinnamamido-1-phenylethyl cinnamate (25)

Colorless solid; mp 181-183° C.; R$_f$=0.52, EtOAc/P.E. 2:3 v/v; [α]$_D$$^{28}$ 59.8 (c 0.5, CHCl$_3$); IR (CHCl$_3$): 3292, 3022, 2927, 2864, 2404, 2358, 1711, 1667, 1630, 1516, 1419, 1327, 1216, 1167, 1095, 1030, 929, 764, 670; $^1$H NMR (200 MHz, CDCl$_3$) δ 7.26-7.82 (m, 17H), 6.30-6.60 (m, 2H), 6.06 (m, 2H), 3.69-4.06 (m, 2H); $^{13}$C NMR (100 MHz, CDCl$_3$) δ 166.5, 166.1, 146.0, 141.6, 137.9, 134.8, 134.2, 130.6, 129.8, 129.0, 128.9, 128.6, 128.3, 127.9, 126.6, 120.4, 117.6, 74.9, 44.9; ESI-LCMS: m/z (M+Na)$^+$ 420.11; HRMS: m/z for C$_{26}$H$_{23}$NO$_3$Na ([M+Na]$^+$): calcd 420.1570, found 420.1566.

Example 26: (R)-2-cinnamamido-1-phenylethyl cinnamate (26)

Colorless solid; mp 183-185° C.; R$_f$=0.52, EtOAc/P.E. 2:3 v/v; [α]$_D$$^{28}$−57.3 (c 0.5, CHCl$_3$); IR (CHCl$_3$): 3292, 3022, 2927, 2864, 2404, 2358, 1711, 1667, 1630, 1516, 1419, 1327, 1216, 1167, 1095, 1030, 929, 764, 670; $^1$H NMR (200 MHz, CDCl$_3$) δ 7.26-7.81 (m, 17H), 6.30-6.59 (m, 2H), 5.99-6.17 (m, 2H), 3.71-4.07 (m, 2H); $^{13}$C NMR (100 MHz, CDCl$_3$) δ 166.5, 166.1, 146.0, 141.6, 137.9, 134.8, 134.3, 130.6, 129.8, 129.0, 128.9, 128.6, 128.3, 127.9, 126.6, 120.4, 117.6, 74.9, 44.9; ESI-LCMS: m/z (M+Na)$^+$ 420.15; HRMS: m/z for C$_{26}$H$_{23}$NO$_3$Na ([M+Na]$^+$): calcd 420.1570, found 420.1562.

Example 27: (S)-1-phenylethane-1,2-diyl (2E,2'E)-bis(3-phenylacrylate) (27)

Colorless solid; mp 131-133° C.; [α]$_D$$^{26}$+42.7 (c 0.5, CHCl$_3$); R$_f$=0.26, EtOAc/P.E. 1:9 v/v; IR (CHCl$_3$): 3022, 1714, 1638, 1436, 1320, 1216, 1166, 767, 671; $^1$H NMR (200 MHz, CDCl$_3$) δ 7.68 (d, J=9.73 Hz, 1H), 7.76 (d, J=9.73 Hz, 1H), 7.28-7.60 (m, 15H), 6.37-6.60 (m, 2H), 6.24 (dd, J=4.55, 7.45 Hz, 1H), 4.44-4.65 (m, 2H); $^{13}$C NMR (50 MHz, CDCl$_3$) δ 166.6, 166.0, 145.6, 145.5, 136.7, 134.2, 130.4, 128.9, 128.7, 128.2, 126.8, 117.7, 117.5, 73.6, 66.2; ESI-LCMS: m/z (M+Na)$^+$ 421.24; HRMS: m/z for C$_{26}$H$_{22}$O$_4$Na ([M+Na]$^+$): calcd 421.1410, found 421.1411.

Example 28: (R)-1-phenylethane-1,2-diyl (2E,2'E)-bis(3-phenylacrylate) (28)

Colorless solid; mp 132-134° C.; [α]$_D$$^{26}$−42.0 (c 0.5, CHCl$_3$); R$_f$=0.26, EtOAc/P.E. 1:9 v/v; IR (CHCl$_3$): 3022, 1714, 1638, 1436, 1320, 1216, 1166, 767, 671; $^1$H NMR (200 MHz, CDCl$_3$) δ 7.68 (d, J=9.73 Hz, 1H), 7.76 (d, J=9.73 Hz, 1H), 7.28-7.60 (m, 15H), 6.37-6.61 (m, 2H), 6.24 (dd, J=4.42, 7.45 Hz, 1H), 4.45-4.66 (m, 2H); $^{13}$C NMR (50 MHz, CDCl$_3$) δ 166.6, 166.0, 145.6, 145.5, 136.7, 134.2, 130.4, 128.9, 128.7, 128.2, 126.8, 117.7, 117.5, 73.6, 66.2; ESI-LCMS: m/z (M+Na)$^+$ 421.17; HRMS: m/z for C$_{26}$H$_{22}$O$_4$Na ([M+Na]$^+$): calcd 421.1410, found 421.1404.

Example 29: (S)-2-cinnamamido-1-(p-tolyl) ethyl cinnamate (29)

Colorless solid; mp 139-140° C.; R$_f$=0.5, EtOAc/P.E. 2:3 v/v; [α]$_D$$^{28}$+55.4 (c 0.5, CHCl$_3$); IR (CHCl$_3$): 3441, 3021, 2926, 2403, 1711, 1669, 1630, 1515, 1438, 1326, 1216, 1168, 1036, 928, 858, 768, 671; $^1$H NMR (200 MHz, CDCl$_3$) δ 7.56-7.79 (m, 2H), 7.13-7.55 (m, 14H), 6.31-6.57 (m, 2H), 5.96-6.16 (m, 2H), 3.73-4.00 (m, 2H), 2.34 (s, 3H); $^{13}$C NMR (100 MHz, CDCl$_3$) δ 166.6, 166.1, 145.8, 141.5, 138.5, 134.9, 134.8, 134.3, 130.6, 129.8, 129.5, 129.0, 128.9, 128.3, 127.9, 126.6, 120.5, 117.7, 74.9, 44.8, 21.3; ESI-LCMS: m/z (M+Na)⁺ 434.07; HRMS: m/z for C₂₇H₂₅NO₃Na ([M+Na]⁺): calcd 434.1727, found 434.1725.

Example 30: (R)-2-cinnamamido-1-(p-tolyl) ethyl cinnamate (30)

Colorless solid; mp 139-141° C.; R$_f$=0.5, EtOAc/P.E. 2:3 v/v; [α]$_D^{28}$–59.6 (c 0.5, CHCl₃); IR (CHCl₃): 3441, 3021, 2926, 2403, 1711, 1669, 1630, 1515, 1438, 1326, 1216, 1168, 1036, 928, 858, 768, 671; ¹H NMR (200 MHz, CDCl₃) δ 7.56-7.79 (m, 2H), 7.13-7.55 (m, 14H), 6.31-6.57 (m, 2H), 5.96-6.16 (m, 2H), 3.73-4.00 (m, 2H), 2.34 (s, 3H); ¹³C NMR (100 MHz, CDCl₃) δ 166.6, 166.0, 145.8, 141.6, 138.5, 134.9, 134.8, 134.3, 130.6, 129.8, 129.5, 129.0, 128.9, 128.3, 127.9, 126.6, 120.4, 117.7, 74.9, 44.8, 21.3; ESI-LCMS: m/z (M+Na)⁺ 434.07; HRMS: m/z for C₂₇H₂₅NO₃Na ([M+Na]⁺): calcd 434.1727, found 434.1721.

Example 31: (S)-1-(p-tolyl) ethane-1,2-diyl (2E, 2'E)-bis(3-phenylacrylate) (31)

Colorless solid; mp 103-105° C.; R$_f$=0.26, EtOAc/P.E. 1:9 v/v; [α]$_D^{27}$ 40.1 (c 0.5, CHCl₃); IR (CHCl₃): 3361, 3164, 3022, 1712, 1634, 1523, 1445, 1401, 1316, 1268, 1215, 1165, 1036, 762, 670; ¹H NMR (400 MHz, CDCl₃) δ 7.65-7.77 (m, 2H), 7.46-7.58 (m, 4H), 7.31-7.43 (m, 8H), 7.20 (d, J=7.79 Hz, 2H), 6.52 (d, 1H, J=16.03 Hz), 6.44 (d, 1H, J=16.03 Hz), 6.20 (dd, J=3.43, 8.01 Hz, 1H), 4.45-4.61 (m, 2H), 2.35 (s, 3H); ¹³C NMR (50 MHz, CDCl₃) δ 166.6, 166.0, 145.5, 138.5, 134.3, 133.7, 130.4, 129.4, 128.9, 128.2, 126.8, 117.8, 117.5, 73.5, 66.2, 21.2; ESI-LCMS: m/z (M+Na)⁺ 435.16; HRMS: m/z for C₂₇H₂₄O₄Na ([M+Na]⁺): calcd 435.1567, found 435.1559.

Example 32: (R)-1-(p-tolyl) ethane-1,2-diyl (2E, 2'E)-bis(3-phenylacrylate) (32)

Colorless solid; mp 103-105° C.; R$_f$=0.26, EtOAc/P.E. 1:9 v/v; [α]$_D^{27}$–42.3 (c 0.5, CHCl₃); IR (CHCl₃): 3361, 3164, 3022, 1712, 1634, 1523, 1445, 1401, 1316, 1268, 1215, 1165, 1036, 762, 670; ¹H NMR (400 MHz, CDCl₃) δ 7.66-7.77 (m, 2H), 7.47-7.57 (m, 4H), 7.32-7.42 (m, 8H), 7.20 (d, J=8.24 Hz, 2H), 6.52 (d, 1H, J=16.03 Hz), 6.44 (d, 1H, J=16.03), 6.20 (dd, J=3.66, 8.24 Hz, 1H), 4.46-4.61 (m, 2H), 2.35 (s, 3H); ¹³C NMR (50 MHz, CDCl₃) δ 166.6, 166.0, 145.5, 138.5, 134.3, 133.7, 130.4, 129.4, 128.9, 128.2, 126.8, 117.8, 117.5, 73.5, 66.2, 21.2; ESI-LCMS: m/z (M+Na)⁺ 435.16; HRMS: m/z for C₂₇H₂₄O₄Na ([M+Na]⁺): calcd 435.1567, found 435.1563.

Example 33: (S)-1-(benzo[d][1,3]dioxol-5-yl)-2-cinnamamidoethyl cinnamate (33)

Colorless solid; mp 186-190° C.; R$_f$=0.23, EtOAc/P.E. 3:7 v/v; [α]$_D^{26}$+42.4 (c 0.53, CHCl₃); IR (CHCl₃): 3361, 3164, 3020, 2932, 2358, 1710, 1666, 1628, 1506, 1444, 1327, 1215, 1167, 1040, 984, 932, 862, 762, 670; ¹H NMR (400 MHz, CDCl₃) δ 7.70 (d, 1H, J=16.03 Hz), 7.62 (d, 1H, J=15.57 Hz), 7.43-7.54 (m, 4H), 7.31-7.40 (m, 6H), 6.89-6.95 (m, 2H), 6.79 (d, J=8.24 Hz, 1H), 6.47 (d, 1H, J=16.03 Hz), 6.39 (d, J=15.57 Hz, 1H), 6.10 (t, J=5.50 Hz, 1H), 5.92-5.98 (m, 3H), 3.75-3.91 (m, 2H); ¹³C NMR (50 MHz, CDCl₃) δ 166.4, 166.0, 147.9, 147.7, 145.9, 141.6, 134.6, 134.1, 131.6, 130.6, 129.7, 128.9, 128.8, 128.2, 127.8, 120.4, 120.2, 117.5, 108.4, 106.9, 101.2, 74.7, 44.7; ESI-LCMS: m/z (M+Na)⁺ 464.16; HRMS: m/z for C₂₇H₂₃NO₅Na ([M+Na]⁺): calcd 464.1468, found 464.1465.

Example 34: (R)-1-(benzo[d][1,3]dioxol-5-yl)-2-cinnamamidoethyl cinnamate (34)

Colorless solid; mp 200-202° C.; R$_f$=0.23, EtOAc/P.E. 3:7 v/v; [α]$_D^{26}$–38.3 (c 0.57, CHCl₃); IR (CHCl₃): 3361, 3164, 3020, 2932, 2358, 1710, 1666, 1628, 1506, 1444, 1327, 1215, 1167, 1040, 984, 932, 862, 762, 670; ¹H NMR (400 MHz, CDCl₃) δ 7.70 (d, 1H, J=16.03 Hz), 7.62 (d, 1H, J=15.57 Hz), 7.44-7.54 (m, 4H), 7.30-7.41 (m, 6H), 6.89-6.94 (m, 2H), 6.79 (d, J=7.79 Hz, 1H), 6.48 (d, J=16.03 Hz, 1H), 6.39 (d, J=15.57 Hz, 1H), 6.10 (t, J=5.72 Hz, 1H), 5.92-5.98 (m, 3H), 3.75-3.91 (m, 2H); ¹³C NMR (50 MHz, CDCl₃) δ 166.4, 166.0, 147.9, 147.7, 145.9, 141.6, 134.6, 134.1, 131.6, 130.6, 129.7, 128.9, 128.8, 128.2, 127.8, 120.4, 120.2, 117.5, 108.4, 106.9, 101.2, 74.7, 44.7; ESI-LCMS: m/z (M+Na)⁺ 464.10; HRMS: m/z for C₂₇H₂₃NO₅Na ([M+Na]⁺): calcd 464.1468, found 464.1467.

Example 35: (S)-1-(benzo[d][1,3]dioxol-5-yl)ethane-1,2-diyl(2E,2'E)-bis(3-phenyl acrylate) (35)

Colorless solid; mp 106-107° C.; R$_f$=0.45, EtOAc/P.E. 1:4 v/v; [α]$_D^{26}$+29.1 (c 0.5, CHCl₃); IR (CHCl₃): 3022, 1714, 1637, 1496, 1446, 1317, 1249, 1215, 1166, 1040, 985, 934, 865, 761, 673, 620; ¹H NMR (200 MHz, CDCl₃) δ 7.67 (d, J=6.32 Hz, 1H), 7.75 (d, J=6.32 Hz, 1H), 7.45-7.58 (m, 4H), 7.31-7.43 (m, 6H), 6.77-6.99 (m, 3H), 6.37-6.57 (m, 2H), 6.13 (dd, J=4.42, 7.71 Hz, 1H), 5.96 (s, 2H), 4.40-4.60 (m, 2H); ¹³C NMR (100 MHz, CDCl₃) δ 166.5, 166.0, 147.9, 147.8, 145.6, 145.5, 134.2, 130.4, 128.9, 128.2, 120.6, 117.6, 117.4, 108.4, 107.3, 101.2, 73.4, 66.2; ESI-LCMS: m/z (M+Na)⁺ 465.14; HRMS: m/z for C₂₇H₂₂O₆Na ([M+Na]⁺): calcd 465.1309, found 465.1307.

Example 36: (R)-1-(benzo[d][1,3]dioxol-5-yl)ethane-1,2-diyl(2E,2'E)-bis(3-phenyl acrylate) (36)

Colorless solid; mp 108-110° C.; R$_f$=0.45, EtOAc/P.E. 1:4 v/v; [α]$_D^{26}$–29.8 (c 0.5, CHCl₃); IR (CHCl₃): 3022, 1714, 1637, 1496, 1446, 1317, 1249, 1215, 1166, 1040, 985, 934, 865, 761, 673, 620; ¹H NMR (400 MHz, CDCl₃) δ 7.66-7.77 (m, 2H), 7.52 (dt, J=2.93, 6.60 Hz, 4H), 7.33-7.43 (m, 6H), 6.88-7.00 (m, 2H), 6.82 (d, J=7.83 Hz, 1H), 6.40-6.55 (m, 2H), 6.13 (dd, J=3.79, 8.19 Hz, 1H), 5.96 (s, 2H), 4.42-4.58 (m, 2H); ¹³C NMR (100 MHz, CDCl₃) δ 166.5, 166.0, 147.9, 147.8, 145.6, 145.5, 134.2, 130.4, 128.9, 128.2, 120.6, 117.6, 117.4, 108.4, 107.3, 101.2, 73.4, 66.2; ESI-LCMS: m/z (M+Na)⁺ 465.26; HRMS: m/z for C₂₇H₂₂O₆Na ([M+Na]⁺): calcd 465.1309, found 465.1306.

Example 37: (S)-1-(benzo[d][1,3]dioxol-4-yl)ethane-1,2-diyl(2E,2'E)-bis(3-phenyl acrylate) (37)

Colorless viscous liquid; R$_f$=0.48, DCM/P.E. 7:3 v/v; [α]$_D^{28}$ 12.9 (c 0.5, CHCl₃); IR (CHCl₃): 3287, 3022, 2923, 2860, 2358, 1716, 1637, 1459, 1317, 1215, 1165, 1040, 987, 934, 855, 761, 672; ¹H NMR (200 MHz, CDCl₃) δ 7.62-7.83 (m, 2H), 7.45-7.60 (m, 4H), 7.29-7.44 (m, 6H), 6.76-6.99 (m, 3H), 6.30-6.61 (m, 2H), 6.02 (d, J=1.14 Hz, 2H), 4.49-4.75 (m, 2H); ¹³C NMR (100 MHz, CDCl₃) δ 166.6, 166.0, 147.7, 145.9, 145.6, 145.1, 134.4, 130.6, 130.5, 129.0, 129.0, 128.3, 128.3, 122.0, 120.1, 118.3, 117.6, 117.6, 108.9, 101.4, 69.3, 64.8; HRMS: m/z for $C_{27}H_{22}O_6Na$ ([M+Na]$^+$): calcd: 465.1309, found 465.1305.

Example 38: (R)-1-(benzo[d][1,3]dioxol-4-yl)ethane-1,2-diyl(2E,2'E)-bis(3-phenyl acrylate) (38)

Colorless viscous liquid; $R_f$=0.48, DCM/P.E. 7:3 v/v; $[\alpha]_D^{28}$ −12.8 (c 0.5, CHCl$_3$); IR (CHCl$_3$): 3287, 3022, 2923, 2860, 2358, 1716, 1637, 1459, 1317, 1215, 1165, 1040, 987, 934, 855, 761, 672; $^1$H NMR (200 MHz, CDCl$_3$) δ 7.62-7.83 (m, 2H), 7.45-7.60 (m, 4H), 7.29-7.44 (m, 6H), 6.76-6.99 (m, 3H), 6.30-6.61 (m, 3H), 6.02 (d, J=1.14 Hz, 2H), 4.49-4.75 (m, 2H); $^{13}$C NMR (100 MHz, CDCl$_3$) δ 166.6, 166.0, 147.7, 145.9, 145.6, 145.1, 134.4, 130.6, 130.5, 129.0, 128.3, 128.3, 122.0, 120.1, 118.3, 117.6, 117.6, 108.9, 101.4, 69.3, 64.8; HRMS: m/z for $C_{27}H_{22}O_6Na$ ([M+Na]$^+$): calcd 465.1309, found 465.1309.

Example 39: (S)-2-benzamido-1-(3,4-dimethoxyphenyl) ethyl benzoate (39)

Colorless solid; mp 129-131° C.; $[\alpha]_D^{28}$+13.1 (c 0.5, CHCl$_3$); $R_f$=0.33, EtOAc/P.E. 1:1 v/v; IR (CHCl$_3$): 3021, 2928, 1717, 1660, 1603, 1520, 1457, 1376, 1320, 1264, 1218, 1152, 1107, 1029, 927, 855, 763, 666; $^1$H NMR (400 MHz, CDCl$_3$) δ 8.05-8.10 (m, 2H), 7.68-7.74 (m, 2H), 7.53-7.60 (m, 1H), 7.36-7.50 (m, 5H), 6.99-7.08 (m, 2H), 6.87 (d, J=8.24 Hz, 1H), 6.63 (t, J=5.50 Hz, 1H), 6.18 (dd, J=4.58, 8.24 Hz, 1H), 3.92-4.08 (m, 2H), 3.88 (s, 3H), 3.87 (s, 3H); $^{13}$C NMR (50 MHz, CDCl$_3$) δ 167.6, 166.3, 149.3, 149.2, 134.3, 133.3, 131.6, 130.2, 129.9, 129.8, 128.6, 128.5, 126.9, 119.0, 111.3, 109.8, 77.7, 77.1, 76.5, 75.2, 56.0, 55.9, 45.2; ESI-LCMS: m/z (M+Na)$^+$ 428.12; HRMS: m/z for $C_{24}H_{23}NO_5Na$ ([M+Na]$^+$): calcd 428.1468, found 428.1462.

Example 40: (R)-2-benzamido-1-(3,4-dimethoxyphenyl) ethyl benzoate (40)

Colorless solid; mp 128-130° C.; $[\alpha]_D^{28}$−13.0 (c 0.5, CHCl$_3$); $R_f$=0.33, EtOAc/P.E. 1:1 v/v; IR (CHCl$_3$): 3021, 2928, 1717, 1660, 1603, 1520, 1457, 1376, 1320, 1264, 1218, 1152, 1107, 1029, 927, 855, 763, 666; $^1$H NMR (400 MHz, CDCl$_3$) δ 8.05-8.11 (m, 2H), 7.68-7.74 (m, 2H), 7.53-7.60 (m, 1H), 7.36-7.50 (m, 5H), 6.98-7.08 (m, 2H), 6.87 (d, J=8.24 Hz, 1H), 6.63 (t, J=5.27 Hz, 1H), 6.18 (dd, J=4.58, 8.24 Hz, 1H), 3.93-4.07 (m, 2H), 3.88 (s, 3H), 3.87 (s, 3H); $^{13}$C NMR (50 MHz, CDCl$_3$) δ 167.7, 166.3, 149.2, 149.2, 134.3, 133.4, 131.6, 130.2, 129.9, 129.8, 128.6, 128.5, 126.9, 119.0, 111.2, 109.7, 77.7, 77.1, 76.5, 75.2, 56.0, 55.9, 45.2; ESI-LCMS: m/z (M+Na)$^+$ 428.12; HRMS: m/z for $C_{24}H_{23}NO_5Na$ ([M+Na]$^+$): calcd 428.1468, found 428.1468.

Example 41: (S)-1-(3,4-dimethoxyphenyl)-2-((E)-3-(3,4,5-trimethoxyphenyl) acrylamido)ethyl (E)-3-(3,4,5-trimethoxyphenyl)acrylate (41)

Colorless solid; mp 138-140° C.; $R_f$=0.42, EtOAc/P.E. 4:1 v/v; $[\alpha]_D^{27}$ 45.4 (c 0.5, CHCl$_3$); IR (CHCl$_3$): 3021, 2932, 2848, 1710, 1669, 1628, 1587, 1511, 1461, 1423, 1326, 1266, 1217, 1138, 1032, 928, 766, 669; $^1$H NMR (200 MHz, CDCl$_3$) δ 7.48-7.71 (m, 2H), 6.83-7.06 (m, 3H), 6.72 (d, J=6.44 Hz, 4H), 6.24-6.47 (m, 2H), 5.96-6.11 (m, 2H), 3.81-3.96 (m, 26H); $^{13}$C NMR (100 MHz, CDCl$_3$) δ 166.6, 166.0, 153.5, 153.5, 149.3, 149.2, 145.8, 141.6, 140.4, 139.7, 130.3, 130.2, 129.7, 119.6, 119.2, 116.8, 111.3, 110.0, 105.4, 105.1, 105.1, 77.5, 77.3, 77.1, 77.0, 76.8, 74.8, 61.0, 56.2, 56.2, 56.1, 56.0, 44.7; HRMS: m/z for $C_{34}H_{39}NO_{11}Na$ ([M+Na]$^+$): calcd 660.2415, found 660.2419.

Example 42: (R)-1-(3,4-dimethoxyphenyl)-2-((E)-3-(3,4,5-trimethoxyphenyl) acrylamido)ethyl (E)-3-(3,4,5-trimethoxyphenyl)acrylate (42)

Colorless solid; mp 138-140° C.; $R_f$=0.42, EtOAc/P.E. 4:1 v/v; $[\alpha]_D^{27}$−43.6 (c 0.5, CHCl$_3$); IR (CHCl$_3$): 3021, 2932, 2848, 1710, 1669, 1628, 1587, 1511, 1461, 1423, 1326, 1266, 1217, 1138, 1032, 928, 766, 669; $^1$H NMR (200 MHz, CDCl$_3$) δ 7.45-7.75 (m, 2H), 6.80-7.12 (m, 3H), 6.72 (d, J=6.32 Hz, 4H), 6.21-6.50 (m, 2H), 6.02 (brs, 2H), 3.72-4.07 (m, 26H); $^{13}$C NMR (100 MHz, CDCl$_3$) δ 166.6, 166.0, 153.5, 153.5, 149.3, 149.2, 145.9, 141.6, 140.4, 139.7, 130.3, 130.2, 129.7, 119.6, 119.2, 116.8, 111.3, 110.0, 105.4, 105.1, 77.6, 77.6, 77.5, 77.3, 77.1, 76.8, 74.8, 61.0, 61.0, 56.2, 56.2, 56.1, 56.0, 44.7; HRMS: m/z for $C_{34}H_{39}NO_{11}Na$ ([M+Na]$^+$): calcd 660.2415, found 660.2407.

Example 43: (S)-1-(3,4-dimethoxyphenyl)-2-(3-phenylpropanamido)ethyl 3-phenyl propanoate (43)

Colorless solid; mp 82-84° C.; $R_f$=0.45, EtOAc/P.E. 1:1 v/v; $[\alpha]_D^{28}$+31.1 (c 0.5, CHCl$_3$); IR (CHCl$_3$): 3313, 3069, 3017, 2926, 2853, 1733, 1658, 1601, 1514, 1455, 1372, 1255, 1230, 1151, 1029, 856, 813, 758, 701, 665; $^1$H NMR (200 MHz, CDCl$_3$) δ 7.07-7.37 (m, 10H), 6.72-6.87 (m, 3H), 5.73 (dd, J=4.23, 8.40 Hz, 1H), 5.37 (brs, 1H), 3.85 (s, 3H), 3.86 (s, 3H), 3.36-3.73 (m, 2H), 2.92 (q, J=6.82 Hz, 4H), 2.66 (t, J=7.39 Hz, 2H), 2.36 (t, J=7.71 Hz, 2H); $^{13}$C NMR (100 MHz, CDCl$_3$) δ 172.2, 172.2, 149.2, 149.1, 140.9, 140.4, 130.2, 128.6, 128.5, 128.4, 128.3, 126.5, 126.4, 126.3, 119.0, 111.2, 109.7, 74.6, 56.0, 44.3, 38.3, 35.8, 31.5, 30.9; HRMS: m/z for $C_{28}H_{31}NO_5Na$ ([M+Na]$^+$): calcd 484.2094, found 484.2092.

Example 44: (R)-1-(3,4-dimethoxyphenyl)-2-(3-phenylpropanamido)ethyl 3-phenyl propanoate (44)

Colorless solid; mp 77-78° C.; $R_f$=0.45, EtOAc/P.E. 1:1 v/v; $[\alpha]_D^{28}$−30.2 (c 0.5, CHCl$_3$); IR (CHCl$_3$): 3313, 3069, 3017, 2926, 2853, 1733, 1658, 1601, 1514, 1455, 1372, 1255, 1230, 1151, 1029, 856, 813, 758, 701, 665; $^1$H NMR (200 MHz, CDCl$_3$) δ 7.10-7.35 (m, 10H), 6.74-6.85 (m, 3H), 5.73 (dd, J=4.29, 8.34 Hz, 1H), 5.30-5.43 (m, 1H), 3.85 (s, 3H), 3.86 (s, 3H), 3.37-3.72 (m, 2H), 2.83-3.00 (m, 4H), 2.60-2.73 (m, 2H), 2.29-2.44 (m, 2H); $^{13}$C NMR (100 MHz, CDCl$_3$) δ 172.2, 172.2, 149.2, 149.1, 140.9, 140.4, 130.2, 128.6, 128.4, 128.3, 126.5, 126.3, 119.0, 111.2, 109.7, 74.6, 56.0, 44.3, 38.3, 35.8, 31.5, 30.9; HRMS: m/z for $C_{28}H_{31}NO_5Na$ ([M+Na]$^+$): calcd 484.2094, found 484.2088.

Example 45: (S)-2-butyramido-1-(3,4-dimethoxyphenyl)ethyl butyrate (45)

Colorless viscous liquid; $R_f$=0.47, EtOAc/P.E. 3:2 v/v; $[\alpha]_D^{26}$ 56.2 (c 0.5, CHCl$_3$); IR (CHCl$_3$): 3449, 3019, 2962, 2404, 1732, 1668, 1600, 1516, 1459, 1372, 1256, 1218, 1172, 1090, 1030, 929, 855, 761, 668; $^1$H NMR (200 MHz, CDCl$_3$) δ 6.78-6.97 (m, 3H), 5.67-5.88 (m, 2H), 3.88 (s, 3H), 3.87 (s, 3H), 3.55-3.74 (m, 2H), 2.26-2.41 (m, 2H), 2.06-2.21 (m, 2H), 1.64 (dsxt, J=4.86, 7.36 Hz, 4H), 0.93 (dt, J=1.45, 7.36 Hz, 6H); $^{13}$C NMR (50 MHz, CDCl$_3$) δ 173.1, 173.0, 149.0, 130.4, 119.0, 111.1, 109.7, 74.2, 55.9, 44.2, 38.6, 36.3, 19.1, 18.4, 13.7, 13.7; ESI-LCMS: m/z (M+Na)⁺ 359.98; HRMS: m/z for $C_{18}H_{27}NO_5Na$ ([M+Na]⁺): calcd 360.1781, found 360.1774.

Example 46: (S)-2-((E)-3-(2-((tert-butyldimethylsilyl)oxy)phenyl)acrylamido)-1-(3,4-dimethoxyphenyl)ethyl (E)-3-(2-((tert-butyldimethylsilyl)oxy)phenyl)acrylate (46)

Light yellow liquid; $R_f$=0.61, EtOAc/P.E. 2:3 v/v; $[\alpha]_D^{26}$ 7.8 (c 0.5, CHCl₃); IR (CHCl₃): 3437, 3021, 2930, 2858, 2402, 1715, 1666, 1628, 1516, 1470, 1260, 1216, 1157, 1031, 922, 841, 762, 669; ¹H NMR (400 MHz, CDCl₃) δ 8.13 (d, J=16.14 Hz, 1H), 7.96 (d, J=15.89 Hz, 1H), 7.46-7.58 (m, 2H), 7.18-7.25 (m, 2H), 6.78-7.02 (m, 7H), 6.46 (d, J=16.14 Hz, 1H), 6.35 (d, J=15.65 Hz, 1H), 5.94-6.02 (m, 1H), 5.85 (t, J=4.77 Hz, 1H), 3.70-3.95 (m, 8H), 0.96-1.10 (m, 18H), 0.12-0.28 (m, 12H); ¹³C NMR (100 MHz, CDCl₃) δ 166.5, 166.1, 154.7, 154.6, 149.1, 149.1, 140.9, 137.0, 131.6, 130.7, 130.4, 130.3, 127.6, 127.5, 126.3, 126.2, 125.7, 121.6, 121.4, 120.2, 120.1, 120.1, 119.9, 119.0, 117.2, 111.1, 109.8, 74.6, 56.1, 55.9, 49.2, 44.6, 34.0, 25.8, 25.8, 24.9, 18.3, −4.2, −4.2; HRMS: m/z for $C_{28}H_{27}NO_5Na$ ([M+Na]⁺): calcd 740.3409, found 740.3381.

Example 47: (S)-2-((E)-3-(3-((tert-butyldimethylsilyl)oxy)phenyl)acrylamido)-1-(3,4-dimethoxyphenyl)ethyl (E)-3-(3-((tert-butyldimethylsilyl)oxy)phenyl)acrylate (47)

Viscous liquid; $R_f$=0.28, EtOAc/P.E. 3:7 v/v; $[\alpha]_D^{27}$+25.4 (c 0.5, CHCl₃); IR (CHCl₃): 3438, 3020, 2938, 2859, 2403, 1713, 1632, 1590, 1516, 1475, 1257, 1218, 1162, 1024, 850, 761, 670; ¹H NMR (500 MHz, CDCl₃) δ 7.66 (d, J=15.87 Hz, 1H), 7.56 (d, J=15.56 Hz, 1H), 7.17-7.29 (m, 2H), 7.09 (d, J=6.71 Hz, 1H), 7.12 (d, J=7.32 Hz, 1H), 6.93-7.03 (m, 4H), 6.79-6.91 (m, 3H), 6.45 (d, J=15.87 Hz, 1H), 6.33 (d, J=15.56 Hz, 1H), 5.99 (br. s., 2H), 3.83-3.95 (m, 8H), 0.99 (s., 18H), 0.20 (s., 12H); ¹³C NMR (125 MHz, CDCl₃) δ 166.5, 165.9, 156.1, 156.0, 149.2, 149.2, 145.7, 141.5, 136.1, 135.6, 130.2, 129.9, 129.7, 122.4, 121.5, 121.0, 120.4, 119.5, 119.3, 119.1, 117.7, 111.2, 109.9, 74.7, 56.0, 55.9, 44.6, 34.0, 25.7, 18.2, −4.4; HRMS: m/z for $C_{28}H_{27}NO_5Na$ ([M+Na]⁺): calcd 740.3409, found 740.3384.

Example 48: (S)-2-((E)-3-(4-((tert-butyldimethylsilyl)oxy)phenyl)acrylamido)-1-(3,4-dimethoxyphenyl)ethyl (E)-3-(4-((tert-butyldimethylsilyl)oxy)phenyl)acrylate (48)

Colorless solid; mp 63-65° C.; $R_f$=0.45, EtOAc/P.E. 2:3 v/v; $[\alpha]_D^{27}$+38.1 (c 0.5, CHCl₃); IR (CHCl₃): 3328, 3019, 2940, 2858, 2405, 1707, 1663, 1602, 1514, 1462, 1424, 1266, 1217, 1160, 1101, 1029, 911, 840, 760, 670; ¹H NMR (500 MHz, CDCl₃) δ 7.67 (d, J=15.87 Hz, 1H), 7.56 (d, J=15.26 Hz, 1H), 7.41 (d, J=8.54 Hz, 2H), 7.37 (d, J=8.54 Hz, 2H), 6.99 (dd, J=1.53, 8.24 Hz, 1H), 6.94-6.96 (m, 1H), 6.78-6.89 (m, 5H), 6.35 (d, J=15.87 Hz, 1H), 6.23 (d, J=15.56 Hz, 1H), 5.98 (dd, J=4.58, 8.24 Hz, 1H), 5.94 (t, J=5.49 Hz, 1H), 3.83-3.93 (m, 8H), 0.98 (m, 18H), 0.21 (m, 12H); ¹³C NMR (125 MHz, CDCl₃) δ 166.8, 166.3, 158.1, 157.4, 149.1, 145.5, 141.2, 130.4, 129.8, 129.4, 128.0, 127.5, 120.5, 120.4, 119.0, 118.1, 115.2, 111.2, 109.9, 74.5, 56.0, 55.9, 44.7, 34.0, 25.6, 24.9, 18.2, −4.4; HRMS: m/z for $C_{28}H_{27}NO_5Na$ ([M+Na]⁺): calcd 740.3409, found 740.3384.

Example 49: (S)-2-cinnamamido-1-(3,4-dimethoxyphenyl)ethyl 3-phenylpropanoate (49)

Colorless solid; mp 101-103° C.; $R_f$=0.34, EtOAc/P.E. 1:1 v/v; $[\alpha]_D^{29}$−13.9 (c 0.5, CHCl₃); IR (CHCl₃): 3444, 3021, 2925, 2858, 2358, 1712, 1670, 1515, 1457, 1371, 1318, 1216, 1163, 1030, 928, 857, 763, 670; ¹H NMR (200 MHz, CDCl₃) δ 7.70 (d, J=16.04 Hz, 1H), 7.46-7.57 (m, 2H), 7.34-7.45 (m, 3H), 7.09-7.33 (m, 5H), 6.77-6.98 (m, 3H), 6.45 (d, J=15.92 Hz, 1H), 5.87 (dd, J=5.18, 7.71 Hz, 1H), 5.72 (t, J=5.31 Hz, 1H), 3.88 (s, 3H), 3.86 (s, 3H), 3.64-3.77 (m, 2H), 2.88-3.01 (m, 2H), 2.41-2.55 (m, 2H); ¹³C NMR (50 MHz, CDCl₃) δ 172.3, 166.4, 149.2, 149.1, 145.8, 140.7, 134.2, 130.6, 130.2, 129.0, 128.6, 128.3, 128.2, 126.3, 119.0, 117.6, 111.1, 109.7, 74.7, 62.6, 56.0, 55.9, 44.4, 38.3, 31.5; ESI-LCMS: m/z (M+Na)⁺ HRMS: m/z $C_{28}H_{29}NO_5Na$ ([M+Na]⁺): calcd 482.1938, found 482.1932.

Example 50: (S)-1-(3,4-dimethoxyphenyl)-2-(3-phenylpropanamido)ethylcinnamate (50)

Colorless solid; mp 112-114° C.; $R_f$=0.45, EtOAc/P.E. 1:1 v/v; $[\alpha]_D^{26}$ 27.2 (c 0.5, CHCl₃); IR (CHCl₃): 3434, 3020, 2926, 2855, 2403, 1733, 1668, 1625, 1514, 1457, 1334, 1217, 1152, 1030, 859, 760, 669; ¹H NMR (200 MHz, CDCl₃) δ 7.61 (d, J=15.66 Hz, 1H), 7.44-7.54 (m, 2H), 7.33-7.42 (m, 3H), 7.14-7.30 (m, 5H), 6.78-6.94 (m, 3H), 6.24 (d, J=15.66 Hz, 1H), 5.86 (dd, J=4.36, 8.27 Hz, 1H), 5.64 (t, J=5.43 Hz, 1H), 3.87 (s, 3H), 3.87 (s, 3H), 3.57-3.82 (m, 2H), 2.89-3.04 (m, 2H), 2.64-2.79 (m, 2H); ¹³C NMR (50 MHz, CDCl₃) δ 172.3, 165.9, 149.2, 149.1, 141.6, 140.3, 134.7, 130.1, 129.8, 128.9, 128.6, 128.3, 127.9, 126.4, 120.2, 119.0, 111.1, 109.8, 74.6, 56.0, 44.5, 35.8, 30.8; ESI-LCMS: m/z (M+Na)⁺ HRMS: m/z for $C_{28}H_{29}NO_5Na$ ([M+Na]⁺): calcd 482.1938, found 482.1934.

Example 51: (S)-2-butyramido-1-(3,4-dimethoxyphenyl)ethyl cinnamate (51)

Colorless solid; mp 93-94° C.; $R_f$=0.45, EtOAc/P.E. 1:1 v/v; $[\alpha]_D^{26}$ 31.5 (c 0.5, CHCl₃); IR (CHCl₃): 3442, 3020, 2927, 2403, 1732, 1668, 1626, 1515, 1458, 1334, 1255, 1216, 1173, 1031, 929, 858, 762, 669; ¹H NMR (500 MHz, CDCl₃) δ 7.62 (d, J=15.56 Hz, 1H), 7.49 (dd, J=2.29, 7.17 Hz, 2H), 7.33-7.40 (m, 3H), 6.83-6.96 (m, 3H), 6.36 (d, J=15.56 Hz, 1H), 5.86-5.93 (m, 2H), 3.87 (s, 3H), 3.89 (s, 3H), 3.72-3.85 (m, 2H), 2.35 (dt, J=1.83, 7.48 Hz, 2H), 1.63-1.69 (m, 2H), 0.92 (t, J=7.32 Hz, 3H); ¹³C NMR (125 MHz, CDCl₃) δ 173.2, 165.9, 149.2, 149.1, 141.6, 134.7, 130.3, 129.8, 128.8, 127.8, 120.2, 119.0, 111.2, 109.8, 77.3, 77.0, 76.8, 74.2, 56.0, 55.9, 44.6, 36.4, 18.4, 13.7; ESI-LCMS: m/z (M+Na)⁺ HRMS: m/z for $C_{23}H_{27}NO_5Na$ ([M+Na]⁺): calcd 420.1781, found 420.1774.

Example 52: (S)-2-cinnamamido-1-(3,4-dimethoxyphenyl)ethyl butyrate (52)

Colorless liquid; 0.28, EtOAc/P.E. 1:1 v/v; $[\alpha]_D^{23}$−2.9 (c 0.5, CHCl₃); ¹H NMR (400 MHz, CDCl₃) δ 7.72 (d, J=16.14 Hz, 1H), 7.53 (dd, J=2.93, 6.60 Hz, 2H), 7.36-7.44 (m, 3H), 6.95-6.99 (dd, J=1.71, 8.07 Hz, 1H), 6.93 (d, J=1.71 Hz, 1H), 6.86 (d, J=8.07 Hz, 1H), 6.49 (d, J=15.89 Hz, 1H), 5.94 (t, J=6.48 Hz, 1H), 5.74-5.85 (m, 1H), 3.80-3.95 (m, 8H), 2.11-2.18 (m, 2H), 1.63 (m, 2H), 0.90-0.94 (m, 3H); IR (CHCl₃): 3446, 3388, 3018, 2966, 1712, 1605, 1516, 1457, 1317, 1257, 1217, 1165, 927, 861, 761, 670; ¹³C NMR (50 MHz, CDCl₃) δ 173.1, 166.5, 149.2, 149.1, 145.8, 134.2, 130.6, 130.2, 129.0, 128.2, 119.0, 117.6, 111.1, 109.8, 74.7, 55.9, 44.3, 38.7, 19.1, 13.7; HRMS: m/z for $C_{28}H_{27}NO_5Na$ ([M+Na]$^+$): calcd 420.1781, found 420.1762.

Example 53: (S)-1-(naphthalen-2-yl)ethane-1,2-diyl (2E,2'E)-bis(3-phenylacrylate) (53)

Colorless solid; mp 120-121° C.; $R_f$=0.48, EtOAc/P.E. 1:4 v/v; $[\alpha]_D^{28}$ –19.5 (c 0.5, CHCl$_3$); IR (CHCl$_3$): 3290, 3022, 2926, 2862, 2404, 2358, 1714, 1637, 1524, 1422, 1318, 1216, 1166, 1030, 929, 763, 671; $^1$H NMR (200 MHz, CDCl$_3$) δ 7.30-8.05 (m, 19H), 6.32-6.68 (m, 3H), 4.51-4.78 (m, 2H); $^{13}$C NMR (100 MHz, CDCl$_3$) δ 166.7, 166.2, 145.8, 145.7, 134.4, 134.2, 133.5, 133.3, 130.6, 130.5, 129.0, 129.0, 128.7, 128.3, 128.2, 127.8, 126.5, 126.3, 124.3, 117.8, 117.6, 73.8, 66.3; ESI-LCMS: m/z (M+Na)$^+$ 471.19; HRMS: m/z for $C_{30}H_{24}O_4Na$ ([M+Na]$^+$): calcd 471.1567, found 471.1566.

Example 54: (R)-1-(naphthalen-2-yl)ethane-1,2-diyl (2E,2'E)-bis (3-phenylacrylate) (54)

Colorless solid; mp 123-124° C.; $R_f$=0.48, EtOAc/P.E. 1:4 v/v; $[\alpha]_D^{28}$ 23.9 (c 0.5, CHCl$_3$); IR (CHCl$_3$): 3290, 3022, 2926, 2862, 2404, 2358, 1714, 1637, 1524, 1422, 1318, 1216, 1166, 1030, 929, 763, 671; $^1$H NMR (200 MHz, CDCl$_3$) δ 7.30-7.96 (m, 19H), 6.34-6.65 (m, 3H), 4.53-4.76 (m, 2H); $^{13}$C NMR (100 MHz, CDCl$_3$) δ 166.7, 166.2, 145.8, 145.7, 134.4, 134.2, 133.5, 133.3, 130.6, 130.5, 129.0, 129.0, 128.7, 128.3, 128.2, 127.8, 126.5, 126.3, 124.3, 117.8, 117.6, 73.8, 66.3; ESI-LCMS: m/z (M+Na)$^+$ 471.16; HRMS: m/z for $C_{30}H_{24}O_4Na$ ([M+Na]$^+$): calcd 471.1567, found 471.1570.

Example 55: (S)-2-cinnamamido-2-(3,4-dimethoxyphenyl)ethyl cinnamate (55)

Colorless solid; mp 117-120° C.; $R_f$=0.47, EtOAc/P.E. 1:1 v/v; $[\alpha]_D^{29}$ 45.9 (c 0.5, CHCl$_3$); IR (CHCl$_3$): 3366, 3021, 2926, 2858, 2405, 2358, 1708, 1630, 1511, 1457, 1321, 1216, 1168, 1029, 928, 762, 670; $^1$H NMR (200 MHz, CDCl$_3$) δ 7.57-7.76 (m, 2H), 7.28-7.55 (m, 10H), 6.79-7.00 (m, 3H), 6.58 (d, J=7.83 Hz, 1H), 6.40 (d, J=8.84 Hz, 1H), 6.48 (d, J=8.59 Hz, 1H), 5.45 (dt, J=4.80, 7.71 Hz, 1H), 4.66 (dd, J=7.71, 11.62 Hz, 1H), 4.43 (dd, J=4.74, 11.56 Hz, 1H), 3.87 (s, 3H), 3.84 (s, 3H); $^{13}$C NMR (50 MHz, CDCl$_3$) δ 167.4, 165.6, 149.2, 148.8, 146.0, 141.7, 134.7, 134.1, 131.0, 130.6, 129.8, 128.9, 128.8, 128.2, 127.9, 120.3, 118.9, 117.2, 111.4, 110.3, 66.2, 55.9, 52.9; HRMS: m/z for $C_{28}H_{27}NO_5Na$ ([M+Na]$^+$): calcd 480.1781, found 480.1776.

Example 56: (S)-1-(3,4-dimethoxyphenyl)ethane-1,2-diyl(2E,2'E)-bis(3-(3,4,5-trimethoxyphenyl)acrylate) (56)

Colorless viscous liquid; $R_f$=0.43, EtOAc/P.E. 1:1 v/v; $[\alpha]_D^{27}$ 33.4 (c 0.5, CHCl$_3$); IR (CHCl$_3$): 3686, 3021, 2937, 2845, 2403, 1712, 1635, 1585, 1510, 1460, 1423, 1319, 1218, 1139, 1032, 928, 766, 670; $^1$H NMR (400 MHz, CDCl$_3$) δ 7.59-7.67 (m, 2H), 7.04 (dd, J=2.29, 8.24 Hz, 1H), 6.97 (d, J=1.83 Hz, 1H), 6.89 (d, J=8.24 Hz, 1H), 6.75 (d, J=6.41 Hz, 4H), 6.32-6.46 (m, 2H), 6.19 (dd, J=3.21, 8.70 Hz, 1H), 4.62 (dd, J=8.93, 12.14 Hz, 1H), 4.47 (dd, J=3.66, 11.91 Hz, 1H), 3.84-3.94 (m, 26H); $^{13}$C NMR (50 MHz, CDCl$_3$) δ 166.6, 166.1, 153.5, 145.5, 140.4, 129.7, 129.1, 119.4, 117.0, 116.7, 111.3, 110.2, 105.4, 73.5, 66.1, 61.0, 56.2, 56.0, 56.0; HRMS: m/z for $C_{34}H_{38}O_{12}Na$ ([M+Na]$^+$): calcd 661.2255, found 661.2252.

Example 57: (S)-1-(3,4,5-trimethoxyphenyl)ethane-1,2-diyl(2E,2'E)-bis(3-(3,4,5-trimethoxyphenyl)acrylate) (57)

Colorless solid; mp 61-62° C.; $R_f$=0.43, EtOAc/P.E. 1:1 v/v; $[\alpha]_D^{29}$ 29.2 (c 0.5, CHCl$_3$); IR (CHCl$_3$): 3290, 3021, 2932, 2404, 2358, 1712, 1634, 1589, 1508, 1460, 1421, 1327, 1217, 1135, 1016, 929, 764, 670; $^1$H NMR (400 MHz, CDCl$_3$) δ 7.58-7.69 (m, 2H), 6.75 (d, J=9.16 Hz, 4H), 6.68 (s, 2H), 6.32-6.48 (m, 2H), 6.16 (dd, J=3.43, 8.93 Hz, 1H), 4.61 (dd, J=8.70, 11.91 Hz, 1H), 4.46 (dd, J=3.43, 11.68 Hz, 1H), 3.82-3.92 (m, 29H); $^{13}$C NMR (50 MHz, CDCl$_3$) δ 166.6, 153.5, 145.8, 140.5, 138.4, 132.1, 129.7, 116.8, 116.6, 105.5, 104.1, 73.8, 61.0, 60.8, 56.2; HRMS: m/z for $C_{35}H_{40}O_{13}Na$ ([M+Na]$^+$): calcd 691.2361, found 691.2354.

Example 58: (S)-1-(3,4,5-trimethoxyphenyl)-2-((E)-3-(3,4,5-trimethoxyphenyl) acrylamido)ethyl (E)-3-(3,4,5-trimethoxyphenyl)acrylate (58)

Colorless solid; mp 67-69° C.; $R_f$=0.28, EtOAc/P.E. 7:3 v/v; $[\alpha]_D^{27}$ 46.6 (c 0.5, CHCl$_3$); IR (CHCl$_3$): 3686, 3441, 3021, 2937, 2403, 1711, 1629, 1589, 1509, 1462, 1424, 1326, 1217, 1136, 1005, 927, 767, 670; $^1$H NMR (200 MHz, CDCl$_3$) δ 7.49-7.71 (m, 2H), 6.62-6.79 (m, 6H), 6.24-6.48 (m, 2H), 5.92-6.08 (m, 2H), 3.79-3.96 (m, 29H); $^{13}$C NMR (50 MHz, CDCl$_3$) δ 166.5, 166.0, 153.5, 153.5, 153.4, 146.0, 141.7, 139.7, 138.1, 133.3, 130.2, 129.6, 119.5, 116.6, 105.4, 105.0, 103.7, 74.9, 61.0, 60.8, 56.3, 56.2, 44.7; ESI-LCMS: m/z (M+Na)$^+$ 690.25; HRMS: m/z for $C_{35}H_{41}NO_{12}Na$ ([M+Na]$^+$): calcd 690.2521, found 690.2516.

Example 59: Characterization Data for Selected Intermediates

1. Intermediate-1: (S)-2-azido-1-(3,4-dimethoxyphenyl)ethyl 3-phenylpropanoate

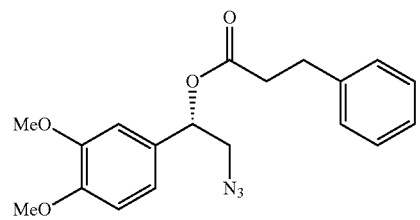 [SMILES: COc1ccc([C@@H](CN=[N+]=[N-])OC(=O)CCc2ccccc2)cc1OC]

Colorless liquid; $[\alpha]_D^{27}$=57.6 (c=0.5, CHCl$_3$); IR (CHCl$_3$): 3347, 3022, 2922, 2104, 1737, 1649, 1516, 1454, 1259, 1217, 1152, 1030, 762, 667; $^1$H NMR (400 MHz, CDCl$_3$) δ 7.15-7.31 (m, 5H), 6.80-6.89 (m, 3H), 5.86 (dd, J=4.12, 8.24 Hz, 1H), 3.87 (s, 3H), 3.88 (s, 3H), 3.61 (dd, J=8.24, 12.82 Hz, 1H), 3.39 (dd, J=4.12, 13.28 Hz, 1H), 2.94-3.02 (m, 2H), 2.64-2.80 (m, 2H); $^{13}$C NMR (50 MHz, CDCl$_3$) δ 171.9, 149.4, 149.1, 140.2, 129.6, 128.5, 128.3, 126.3, 119.1, 111.2, 109.7, 74.6, 56.0, 55.1, 35.9, 30.8.

2. Intermediate-2: (S)-2-azido-1-(3,4-dimethoxyphenyl)ethyl cinnamate

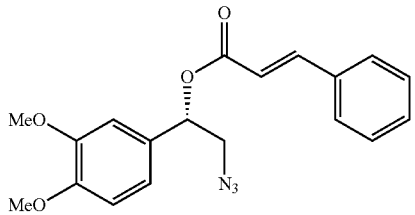 [SMILES: COc1ccc([C@@H](CN=[N+]=[N-])OC(=O)/C=C/c2ccccc2)cc1OC]

Pale yellow liquid; $[\alpha]_D^{27}$=49.0 (c=0.5, CHCl$_3$); IR (CHCl$_3$): 3351, 3021, 2402, 1663, 1621, 1516, 1431, 1217, 1153, 1029, 928, 763, 670; $^1$H NMR (200 MHz, CDCl$_3$) δ 7.75 (d, J=15.92 Hz, 1H), 7.54 (dd, J=3.03, 6.44 Hz, 2H), 7.33-7.46 (m, 3H), 6.80-7.07 (m, 3H), 6.51 (d, J=15.92 Hz, 1H), 5.98 (dd, J=4.17, 7.83 Hz, 1H), 3.87 (s, 3H), 3.91 (s, 3H), 3.62-3.79 (m, 1H), 3.52 (dd, J=4.17, 13.01 Hz, 1H), 1.60 (br. s., 1H), 1.26 (s, 1H); $^{13}$C NMR (50 MHz, CDCl$_3$) δ 165.9, 149.4, 149.2, 146.0, 134.2, 130.6, 129.8, 129.0, 128.2, 119.1, 117.4, 111.2, 109.7, 74.6, 56.0, 56.0, 55.3.

3. Intermediate-3: benzyl (S)-(1-(3,4-dimethoxyphenyl)-2-hydroxyethyl)carbamate

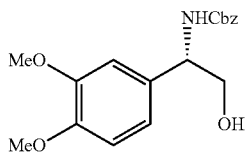

Light brown solid; $[\alpha]_D^{27}$=26.7 (c=0.5, CHCl$_3$); IR (CHCl$_3$): 3433, 3022, 2927, 2403, 1713, 1601, 1509, 1457, 1257, 1217, 1154, 1034, 927, 764, 669; $^1$H NMR (200 MHz, CDCl$_3$) δ 7.25-7.42 (m, 5H), 6.77-6.87 (m, 3H), 5.54 (d, J=5.05 Hz, 1H), 5.09 (s, 2H), 4.70-4.84 (m, 1H), 3.78-3.90 (m, 8H), 2.34 (brs, 1H), 1.75 (br. s., 1H); $^{13}$C NMR (50 MHz, CDCl$_3$) δ 156.5, 149.2, 148.6, 136.3, 131.7, 128.6, 128.2, 118.6, 111.4, 109.9, 67.1, 66.4, 56.9, 56.0, 55.9.

4. Intermediate-4: (S)-2-amino-2-(3,4-dimethoxyphenyl)ethan-1-ol

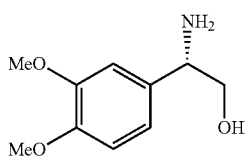

$^1$H NMR (200 MHz, CDCl$_3$) δ 6.77-6.96 (m, 3H), 4.02 (brs, 1H), 3.86 (s, 3H), 3.88 (s, 3H), 3.69 (brs, 1H), 3.47-3.64 (m, 1H), 2.33 (brs, 2H); $^{13}$C NMR (50 MHz, CDCl$_3$) δ 149.1, 148.4, 118.6, 111.2, 109.8, 67.8, 57.1, 55.9.

5. Intermediate-5: (S)-2-azido-1-(3,4-dimethoxyphenyl)ethyl butyrate

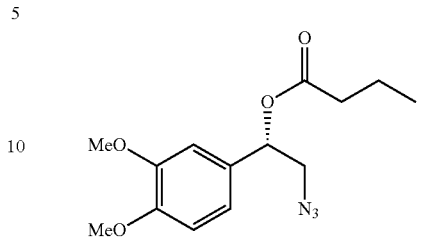

Colorless liquid; $[\alpha]_D^{27}$=89.7 (c=0.5, CHCl$_3$); IR (CHCl$_3$): 3347, 3022, 2925, 2402, 2104, 1736, 1602, 1519, 1427, 1216, 1170, 1029, 929, 764, 670; $^1$H NMR (400 MHz, CDCl$_3$) δ 6.83-6.94 (m, 3H), 5.87 (dd, J=3.66, 8.24 Hz, 1H), 3.87 (s, 3H), 3.89 (s, 3H), 3.63 (dd, J=8.24, 13.28 Hz, 1H), 3.42 (dd, J=4.12, 13.28 Hz, 1H), 2.38 (dt, J=1.83, 7.33 Hz, 2H), 1.69 (sxt, J=7.42 Hz, 2H), 0.95 (t, J=7.33 Hz, 3H); $^{13}$C NMR (50 MHz, CDCl$_3$) δ 172.6, 149.3, 149.1, 129.8, 119.0, 111.1, 109.6, 74.3, 55.9, 55.2, 36.3, 18.4, 13.7.

Example 60: Bio Evaluation of Synthesized Compounds

1) Test Model cultures of Chloroquine-sensitive (3D7) and resistant (K1) strains of *P. falciparum* are routinely maintained in medium RPNI supplemented with 25 mM HEPES, 0.2% D-glucose, 0.21% sodium bicarbonate and 0.5% ALBU-MAX-II (Srivastava & Puri, 2004). The stock (5 mg/mL or 10 mM) solutions of extracts were prepared in DMSO and required dilutions were made in culture medium. For evaluation of 50% Inhibitory concentration (IC$_{50}$) of the compounds, Malaria SYBR Green I-based fluorescence (MSF) assay was carried out (Singh et al 2011).

2) Assay Protocol

Two-fold serial dilutions of test samples were made in 96 well plates and incubated with 1.0% parasitized cell suspension containing 0.8% parasitaemia (Asynchronous culture with more than 80% ring stages). The plates were incubated at 37° C. in CO$_2$ incubator in an atmosphere of 5% CO$_2$ and air mixture. 72 hours later 100 µL of lysis buffer containing 2× concentration of SYBR Green-I (Invitrogen) was added to each well and incubated for one hour at 37° C. The plates were examined at 485±20 nm of excitation and 530±20 nm of emission for relative fluorescence units (RFUs) per well using the fluorescence plate reader (FLX800, BIOTEK). IC$_{50}$ values were obtained by Logit regression analysis of dose response curves (Singh et al. 2011). Chloroquine was used as the standard reference drug.

Criteria for Selection of Lead Molecule

IC$_{50}$≤10.0 µg/ml for crude extracts and fractions and ≤1.0 µM for single molecule 3) Cytotoxicity Assay Cytotoxicity of the samples was carried out using Vero cell line (C1008; Monkey kidney fibroblast) following the method as mentioned in Sashidhara et al. (2012). The cells were incubated with test sample dilutions for 72 h and MTT was used as reagent for detection of cytotoxicity. Podophyllotoxin (SIGMA) was used as the standard reference drug. 50% cytotoxic concentration (CC$_{50}$) was determined using non-linear regression analysis of dose response curves. Selectivity Index (SI) was calculated as:

$SI = CC_{50}/IC_{50}$

Criteria for Selection $SI = CC_{50}/IC_{50} = >10.0$ for crude extracts and fractions and >50.0 for single molecule 4) In Vivo Evaluation:
Test Technique—

Five synthetic molecules were evaluated against chloroquine resistant *P. yoelii* (N-67) Swiss mice model. The molecules were tested at 100 mg/kg dose through intraperitoneal route. The mice received infective inoculum containing $1 \times 10^5$ parasites on day 0 and then received four doses of test compound on day 0-3 once daily. Five infected mice were used for each molecule and five infected mice were kept as untreated control. Arteether (5 mg/kg, ×4, intramuscular) was used as positive control. Thin blood smear from tail blood of each mouse was prepared on day 4. The blood smears were fixed in methanol, stained with Giemsa's stain and examined under the light microscope (100×oil immersion). At least 10-15 fields per smear were scanned to obtain percent parasitaemia in treated as well as untreated mice. If significant suppression in percent parasitaemia is observed on day 4, the monitoring continues up to day 28.

TABLE 1a

In vitro antimalarial activity of nitrogen analogues (with different substituents on aromatic aldehyde) of Syncarpamide

| Nitrogen analogue | $IC_{50}$ (μg/ml)/(μM) against | | $CC_{50}$ (μg/ml/(μM) |
|---|---|---|---|
| | 3D7 | K1 | |
| 1 (Syncarpamide) | 3.9 | 2.56 | 80.66 |
| 2 | >5.0 | nd | 66.67 |
| 5 | 6.69 | 3.64 | 66.74 |
| 6 | >5.0 | nd | 5.08 |
| 9 | >5.0 | >5.0 | 77.81 |
| 10 | >5.0 | nd | 117.47 |
| 13 | >5.0 | nd | 147.72 |
| 14 | >5.0 | nd | 62.73 |
| 17 | >5.0 | nd | 153.0 |
| 18 | >5.0 | nd | >200 |
| 21 | >5.0 | nd | >200 |
| 22 | >5.0 | >5.0 | 194.08 |
| 25 | 3.85 | >10.0 | 31.69 |
| 26 | 4.72 | >10.0 | 63.88 |
| 29 | 6.77 | >10.0 | 140.67 |
| 30 | 6.97 | >10.0 | 49.36 |
| 33 | >5.0 | >5.0 | 189.61 |
| 34 | >5.0 | nd | >200 | nd:- Not detected

TABLE 1b

In vitro antimalarial activity of nitrogen analogues (with different acid chains) of syncarpamide

| Nitrogen analogue | $IC_{50}$ (μg/ml)/(μM) against | | $CC_{50}$ (μg/ml/(μM) |
|---|---|---|---|
| | 3D7 | K1 | |
| 39 | 6.67 | >10.0 | 8.16 |
| 40 | 3.66 | >10.0 | 103.76 |
| 41 | 3.16 | 1.78 | 87.98 |
| 42 | 2.28 | 2.07 | 88.94 |
| 43 | 2.86 | >10.0 | 39.34 |
| 44 | 5.86 | >10.0 | 73.19 |
| 45 | >10.0 | >10.0 | 51.84 |
| 46 | 8.49 | 4.56 | 58.91 |
| 47 | >10.0 | 7.52 | 52.62 |
| 48 | 7.92 | 3.37 | 40.79 |
| 49 | >10.0 | >10.0 | 36.9 |
| 50 | >10.0 | >10.0 | 44.29 |
| 51 | >10.0 | >10.0 | 42.43 |
| 52 | >10.0 | >10.0 | 29.89 |
| 55 | >10.0 | >10.0 | 55.59 |
| 58 | 1.89 | 1.93 | 42.68 |
| CQ | 0.005 ± 0.0 | 0.25 ± 0.020 | 75 |

TABLE 2

In vitro antimalarial activity of oxygen analogues of syncarpamide

| Nitrogen analogue | $IC_{50}$ (μg/ml)/(μM) against | | $CC_{50}$ (μg/ml/(μM) |
|---|---|---|---|
| | 3D7 | K1 | |
| 3 | >5.0 | nd | 24.29 |
| 4 | >5.0 | >5.0 | 5.87 |
| 7 | 3.37 | 3.47 | 6.44 |
| 8 | >5.0 | nd | 121.81 |
| 11 | 3.8 | 3.23 | 14.04 |
| 12 | >5.0 | nd | 51.69 |
| 15 | >5.0 | nd | 61.89 |
| 16 | >5.0 | nd | 22.31 |
| 19 | >5.0 | nd | 33.49 |
| 20 | >5.0 | nd | 23.27 |
| 23 | >5.0 | nd | 28.43 |
| 24 | >5.0 | nd | 82.74 |
| 27 | >5.0 | nd | 39.15 |
| 28 | >5.0 | nd | 30.33 |
| 31 | >5.0 | >5.0 | >200 |
| 32 | >5.0 | nd | >200 |
| 35 | >5.0 | nd | 31.79 |
| 36 | >5.0 | nd | 56.64 |
| 37 | >10.0 | >10.0 | >200 |
| 38 | 7.42 | >10.0 | >200 |
| 53 | >10.0 | >10.0 | >200 |
| 54 | >10.0 | 2.15 | 180.94 |
| 56 | 2.34 | 2.62 | 55.70 |
| 57 | 6.29 | 2.23 | 47.38 |
| CQ | 0.005 ± 0.0 | 0.25 ± 0.020 | 75 | nd:- Not detected

TABLE 3

In vivo antimalarial activity of selected molecules

| Sr. | Compound | % parasitaemia on day 4 in 5 individual mice | | | | |
|---|---|---|---|---|---|---|
| 1 | 1 (Syncarpamide) | 09.50 | 13.76 | 11.93 | 11.72 | 13.20 |
| 2 | 41 | 11.78 | 11.93 | 11.12 | 11.26 | 12.13 |
| 3 | 42 | 14.07 | 12.50 | 15.10 | 12.16 | 11.46 |
| 4 | 56 | 06.06 | 08.31 | 16.23 | 13.92 | 11.13 |
| 5 | 58 | 10.10 | 10.16 | 13.50 | 07.50 | 11.92 |
| 6 | Untreated | 11.40 | 13.60 | 16.16 | 09.80 | 10.06 |
| | Arteether | 0.0 | 0.0 | 0.0 | 0.0 | 0.0 |

ADVANTAGES OF THE INVENTION a. Novel Anti-malarial agents
b. Novel chemical route for synthesis
c. High yields

The invention claimed is:
1. A compound of formula (I)

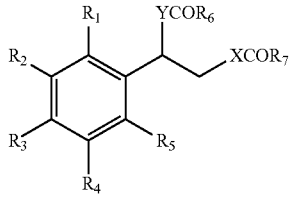

Formula (I)

wherein, X is selected from O and NH;
R₁, R₂, R₃, R₄ and R₅ is selected from H, CH₃, and OMe, or R₁ and R₂ or R₂ and R₃ or R₃ and R₄ or R₄ and R₅ may be combined to form a 5 or 6 membered saturated or unsaturated ring optionally having one or more hetero atoms;
Y is selected from O and NH and
R₆, R₇ is selected from

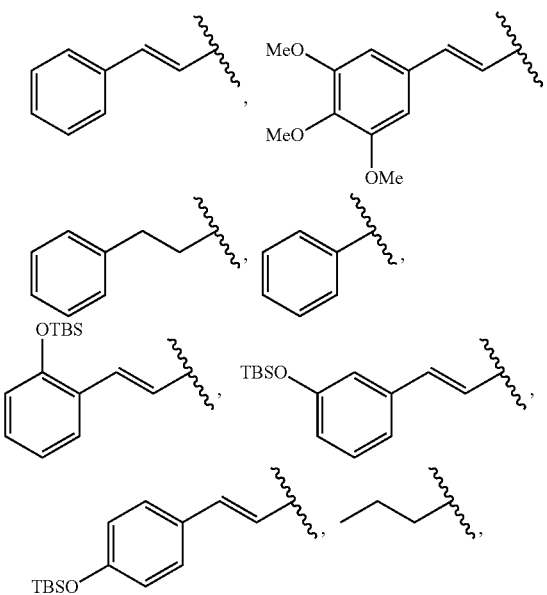

and a pharmaceutically acceptable salt thereof
with the proviso that when R6 is

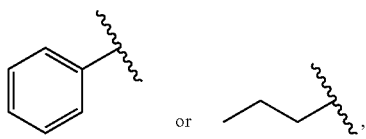

then X is NH, and TBS refers to Tert-butyldimethyl silyl; and
wherein said compound is selected from
(R)-2-cinnamamido-1-(3,4-dimethoxyphenyl)ethylcinnamate,
(S)-1-(3,4-dimethoxyphenyl)ethane-1,2-diyl(2E,2'E)-bis(3-phenylacrylate),
(R)-1-(3,4-dimethoxyphenyl)ethane-1,2-diyl(2E,2'E)-bis(3-phenylacrylate),
(S)-2-cinnamamido-1-(3,4,5-trimethoxyphenyl) ethyl cinnamate,
(R)-2-cinnamamido-1-(3,4,5-trimethoxyphenyl)ethyl cinnamate,
(S)-1-(3,4,5-trimethoxyphenyl)ethane-1,2-diyl (2E,2'E)-bis(3-phenylacrylate),
(R)-1-(3,4,5-trimethoxyphenyl)ethane-1,2-diyl(2E,2'E)-bis(3-phenylacrylate),
(S)-2-cinnamamido-1-(2-methoxyphenyl)ethylcinnamate,
(R)-2-cinnamamido-1-(2-methoxyphenyl)ethylcinnamate,
(S)-1-(2-methoxyphenyl)ethane-1,2-diyl(2E,2'E)-bis(3-phenylacrylate),
(R)-1-(2-methoxyphenyl)ethane-1,2-diyl(2E,2'E)-bis(3-phenylacrylate),
(S)-2-cinnamamido-1-(3-methoxyphenyl)ethyl cinnamate,
(R)-2-cinnamamido-1-(3-methoxyphenyl)ethylcinnamate,
(S)-1-(3-methoxyphenyl)ethane-1,2-diyl (2E,2'E)-bis(3-phenylacrylate),
(R)-1-(3-methoxyphenyl)ethane-1,2-diyl(2E,2'E)-bis(3-phenylacrylate),
(S)-2-cinnamamido-1-(4-methoxyphenyl)ethyl cinnamate,
(R)-2-cinnamamido-1-(4-methoxyphenyl)ethylcinnamate,
(S)-1-(4-methoxyphenyl)ethane-1,2-diyl (2E,2'E)-bis(3-phenylacrylate),
(R)-1-(4-methoxyphenyl)ethane-1,2-diyl(2E,2'E)-bis(3-phenylacrylate),
(S)-2-cinnamamido-1-(2,3-dimethoxyphenyl)ethyl cinnamate,
(R)-2-cinnamamido-1-(2,3-dimethoxyphenyl)ethyl cinnamate,
(S)-1-(2,3-dimethoxyphenyl)ethane-1,2-diyl(2E,2'E)-bis(3-phenylacrylate),
(R)-1-(2,3-dimethoxyphenyl)ethane-1,2-diyl(2E,2'E)-bis(3-phenylacrylate),
(S)-2-cinnamamido-1-phenylethyl cinnamate,
(R)-2-cinnamamido-1-phenylethyl cinnamate,
(S)-1-phenylethane-1,2-diyl(2E,2'E)-bis(3-phenylacrylate),
(R)-1-phenylethane-1,2-diyl (2E,2'E)-bis(3-phenylacrylate),
(S)-2-cinnamamido-1-(p-tolyl)ethyl cinnamate,
(R)-2-cinnamamido-1-(p-tolyl)ethylcinnamate,
(S)-1-(p-tolyl)ethane-1,2-diyl (2E,2'E)-bis(3-phenylacrylate),
(R)-1-(p-tolyl)ethane-1,2-diyl(2E,2'E)-bis(3-phenylacrylate),
(S)-1-(benzo[d][1,3]dioxol-5-yl)-2-cinnamamidoethyl-cinnamate,
(R)-1-(benzo[d][1,3]dioxol-5-yl)-2-cinnamamidoethyl-cinnamate,
(S)-1-(benzo[d][1,3]dioxol-5-yl)ethane-1,2-diyl(2E,2'E)-bis(3-phenylacrylate),
(R)-1-(benzo[d][1,3]dioxol-5-yl)ethane-1,2-diyl (2E,2'E)-bis(3-phenylacrylate),
(S)-1-(benzo[d][1,3]dioxol-4-yl)ethane-1,2-diyl (2E,2'E)-bis(3-phenylacrylate),
(R)-1-(benzo[d][1,3]dioxol-4-yl)ethane-1,2-diyl (2E,2'E)-bis(3-phenylacrylate), (S)-2-benzamido-1-(3,4-dimethoxyphenyl)ethyl benzoate, (R)-2-benzamido-1-(3,4-dimethoxyphenyl)ethyl benzoate, (S)-1-(3,4-dimethoxyphenyl)-2-((E)-3-(3,4,5-trimethoxyphenyl)acrylamido)ethyl(E)-3-(3,4,5-trimethoxyphenyl)acrylate, (R)-1-(3,4-dimethoxyphenyl)-2-((E)-3-(3,4,5-trimethoxyphenyl)acrylamido)ethyl(E)-3-(3,4,5-trimethoxyphenyl)acrylate, (S)-1-(3,4-dimethoxyphenyl)-2-(3-phenylpropanamido)ethyl-3-phenylpropanoate, (R)-1-(3,4-dimethoxyphenyl)-2-(3-phenylpropanamido)ethyl-3-phenylpropanoate, (S)-2-butyramido-1-(3,4-dimethoxyphenyl)ethylbutyrate, (S)-2-((E)-3-(2-((tert-butyldimethylsilyl)oxy)phenyl)acrylamido)-1-(3,4-dimethoxyphenyl)ethyl(E)-3-(2-((tert-butyldimethylsilyl)oxy)phenyl)acrylate;

(S)-2-((E)-3-(3-((tert-butyldimethylsilyl)oxy)phenyl)acrylamido)-1-(3,4-dimethoxyphenyl)ethyl(E)-3-(3-((tert-butyldimethylsilyl)oxy)phenyl)acrylate, (S)-2-((E)-3-(4-((tert-butyldimethylsilyl)oxy)phenyl)acrylamido)-1-(3,4-dimethoxy phenyl)ethyl(E)-3-(4-((tert-butyldimethylsilyl)oxy)phenyl)acrylate, (S)-2-cinnamamido-1-(3,4-dimethoxyphenyl)ethyl3-phenylpropanoate, (S)-1-(3,4-dimethoxyphenyl)-2-(3-phenylpropanamido)ethylcinnamate, (S)-2-butyramido-1-(3,4-dimethoxyphenyl)ethylcinnamate, (S)-2-cinnamamido-1-(3,4-dimethoxyphenyl)ethyl butyrate, (S)-1-(naphthalen-2-yl)ethane-1,2-diyl (2E,2'E)-bis(3-phenylacrylate), (R)-1-(naphthalen-2-yl)ethane-1,2-diyl (2E,2'E)-bis(3-phenylacrylate), (S)-2-cinnamamido-2-(3,4-dimethoxyphenyl)ethylcinnamate, (S)-1-(3,4-dimethoxyphenyl)ethane-1,2-diyl(2E,2'E)-bis(3-(3,4,5-trimethoxyphenyl)acrylate), (S)-1-(3,4,5-trimethoxyphenyl)ethane-1,2-diyl(2E,2'E)-bis(3-(3,4,5-trimethoxyphenyl)acrylate), and (S)-1-(3,4,5-trimethoxyphenyl)-2-((E)-3-(3,4,5-trimethoxyphenyl)acrylamido)ethyl(E)-3-(3,4,5-trimethoxyphenyl)acrylate.

2. The compounds as claimed in claim 1, wherein said compounds are useful as anti-malarial agents.

3. A pharmaceutical composition comprising the compound of formula (I) as claimed in claim 1 and at least one pharmaceutically acceptable carrier.

4. A method for treating or preventing a malaria infection in a subject, which comprises administering a therapeutically effective amount of the compound of formula (I) as claimed in claim 1 and at least one pharmaceutically acceptable carrier or diluent or excipient.

5. The method as claimed in claim 4, wherein said subject is human.

6. A process for the preparation of compounds of formula (I)

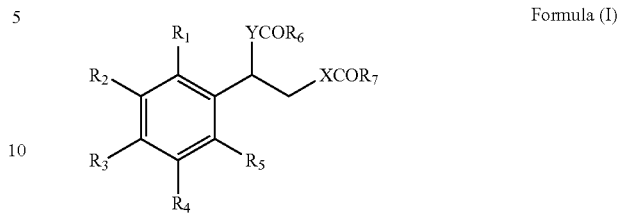

Formula (I)

wherein, X is selected from O and NH;

$R_1$, $R_2$, $R_3$, $R_4$ and $R_5$ is selected from H, $CH_3$, and OMe, or $R_1$ and $R_2$ or $R_2$ and $R_3$ or $R_3$ and $R_4$ or $R_4$ and $R_5$ may be combined to form a 5 or 6 membered saturated or unsaturated ring optionally having one or more hetero atoms;

Y is selected from O and NH and $R_6$, $R_7$ is selected from

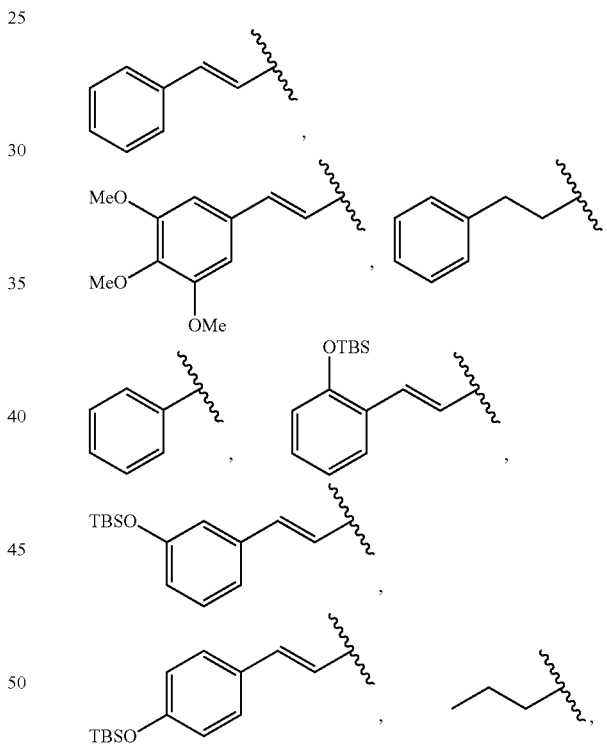

and a pharmaceutically acceptable salt thereof with the proviso that when R6 is

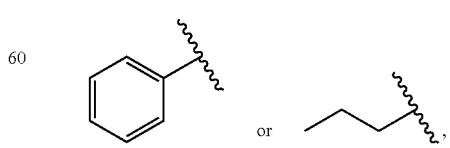

then X is NH, and TBS refers to Tert-butyldimethyl silyl wherein said process comprises the steps of:

a) subjecting the styrene compound of formula B

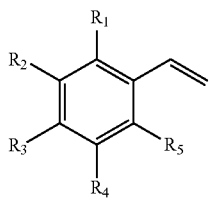
B to dihydroxylation at 0° C. for the period ranging from 6 to 24 h to obtain the diol compound of formula C

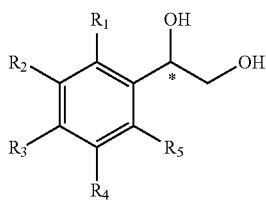
C b) subjecting the diol compound of formula C of step (a) to monotosylation at 0° C. for the period ranging from 3 to 4 h to obtain the monotosylated compound of formula D

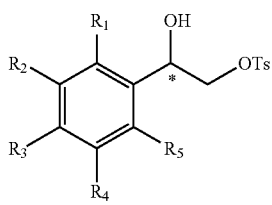
D c) treating the monotosylated compound of formula D of step (b) with sodium azide to obtain the azido alcohol of formula E

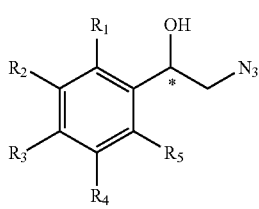
E d) reducing the azido alcohol of formula E of step (c) with anhydrous MeOH and palladium on carbon to furnish the amino alcohol of formula F

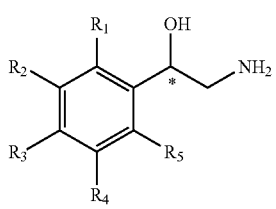
F e) coupling the amino alcohol of formula F of step (d) or diol compound of formula C of step (a) with carboxylic acid in presence of DCC (N,N'-dicyclohexylcarbodiimide) and DMAP (4-Dimethylaminopyridine) to obtain the compound of formula I.

7. The process as claimed in claim 6, wherein said styrene compounds in step (a) are selected from

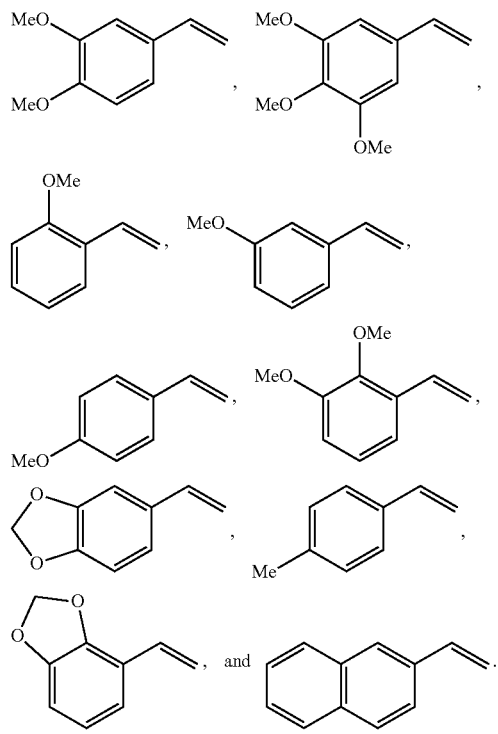

8. The process as claimed in claim 6, wherein said acid compounds in step (e) are selected from

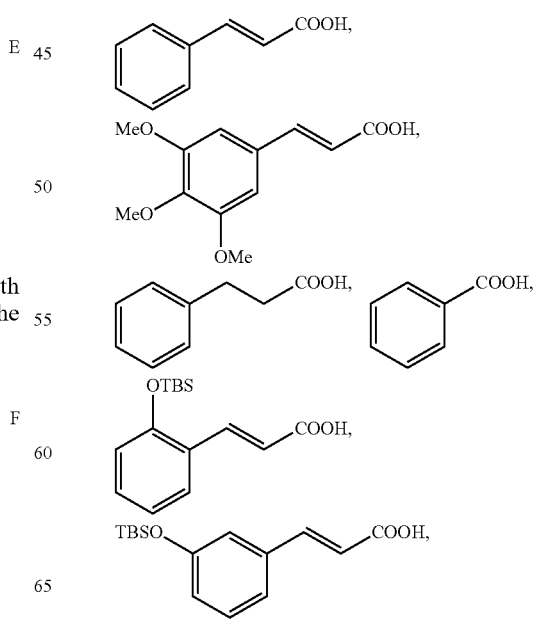

-continued
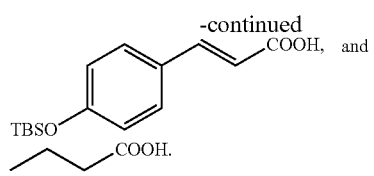

UNITED STATES PATENT AND TRADEMARK OFFICE
CERTIFICATE OF CORRECTION

PATENT NO. : 10,519,098 B2
APPLICATION NO. : 15/520989
DATED : December 31, 2019
INVENTOR(S) : Asish Kumar Bhattacharya et al.

Page 1 of 2

It is certified that error appears in the above-identified patent and that said Letters Patent is hereby corrected as shown below:

On the Title Page

Column 2 (Abstract), Line 3, "$R_1$, $R_2$, $R_3$, $R_4$ and $R_5$is selected from" should be --$R_1$, $R_2$, $R_3$, $R_4$ and $R_5$ are selected from--.

Column 2 (Abstract), Lines 5-8, "O or NH and $R_6$, $R_7$ is selected from the following compounds: or pharmaceutically acceptable salts thereof," should be --O or NH and $R_6$, $R_7$ are selected from the following compounds or pharmaceutically acceptable salts thereof;--.

In the Specification

Column 1, Line 27, "SA Ross et l." should be --SA Ross et al.--.

Column 2, Line 41, "$R_1$, $R_2$, $R_3$, $R_4$ and $R_5$ is selected from" should be --$R_1$, $R_2$, $R_3$, $R_4$ and $R_5$ are selected from--.

Column 2, Line 43, "combined to form 5 to 6 membered" should be --combined to form a 5 to 6 membered--.

Column 2, Line 46, "$R_6$, $R_7$ is selected from" should be --$R_6$, $R_7$ are selected from--.

Column 3, Line 41, "$R_1$, $R_2$, $R_3$, $R_4$ and $R_5$ is selected from" should be --$R_1$, $R_2$, $R_3$, $R_4$ and $R_5$ are selected from--.

Column 3, Line 43, "combined to form 5 to 6 membered" should be --combined to form a 5 to 6 membered--.

Column 3, Line 46, "$R_6$, $R_7$ is selected from" should be --$R_6$, $R_7$ are selected from--.

Column 4, Line 11, "formula (I) are selected from" should be --formula (I) is selected from--.

Signed and Sealed this
Second Day of June, 2020

Andrei Iancu
*Director of the United States Patent and Trademark Office*

In the Claims

Column 47, Line 16 (Claim 1), "$R_1$, $R_2$, $R_3$, $R_4$ and $R_5$ is selected from" should be --$R_1$, $R_2$, $R_3$, $R_4$ and $R_5$ are selected from--.

Column 47, Line 22 (Claim 1), "$R_6$, $R_7$ is selected from" should be --$R_6$, $R_7$ are selected from--.

Column 50, Line 16 (Claim 6), "$R_1$, $R_2$, $R_3$, $R_4$ and $R_5$ is selected from" should be --$R_1$, $R_2$, $R_3$, $R_4$ and $R_5$ are selected from--.

Column 50, Line 22 (Claim 6), "$R_6$, $R_7$ is selected from" should be --$R_6$, $R_7$ are selected from--.